(12) United States Patent
Tan et al.

(10) Patent No.: US 12,257,263 B2
(45) Date of Patent: Mar. 25, 2025

(54) PHARMACEUTICAL COMPOSITIONS FOR DEMODEX RELATED BLEPHARITIS AND EYELID CRUSTING

(71) Applicant: Tarsus Pharmaceuticals, Inc., Irvine (CA)

(72) Inventors: Tiang Hin Jerry Tan, Singapore (SG); Yong Ming Por, Singapore (SG)

(73) Assignee: Tarsus Pharmaceuticals, Inc., Irvine, CA (US)

( * ) Notice: Subject to any disclaimer, the term of this patent is extended or adjusted under 35 U.S.C. 154(b) by 15 days.

(21) Appl. No.: 17/570,745

(22) Filed: Jan. 7, 2022

(65) Prior Publication Data
US 2022/0125817 A1 Apr. 28, 2022

Related U.S. Application Data

(63) Continuation of application No. 16/725,761, filed on Dec. 23, 2019, now abandoned, which is a continuation of application No. 15/501,420, filed as application No. PCT/SG2014/000371 on Aug. 4, 2014, now abandoned.

(51) Int. Cl.
| | | |
|---|---|---|
| A61K 31/7048 | (2006.01) | |
| A61K 9/00 | (2006.01) | |
| A61K 9/06 | (2006.01) | |
| A61K 9/107 | (2006.01) | |
| A61K 31/65 | (2006.01) | |
| A61K 45/06 | (2006.01) | |
| A61K 47/06 | (2006.01) | |
| A61K 47/10 | (2017.01) | |
| A61K 47/14 | (2017.01) | |
| A61K 47/18 | (2017.01) | |
| A61K 47/22 | (2006.01) | |
| A61K 47/24 | (2006.01) | |
| A61K 47/26 | (2006.01) | |
| A61K 47/34 | (2017.01) | |
| A61K 47/44 | (2017.01) | |

(52) U.S. Cl.
CPC ........ *A61K 31/7048* (2013.01); *A61K 9/0014* (2013.01); *A61K 9/0048* (2013.01); *A61K 9/06* (2013.01); *A61K 9/107* (2013.01); *A61K 31/65* (2013.01); *A61K 45/06* (2013.01); *A61K 47/06* (2013.01); *A61K 47/10* (2013.01); *A61K 47/14* (2013.01); *A61K 47/183* (2013.01); *A61K 47/22* (2013.01); *A61K 47/24* (2013.01); *A61K 47/26* (2013.01); *A61K 47/34* (2013.01); *A61K 47/44* (2013.01)

(58) Field of Classification Search
CPC .............. A61K 31/7048; A61K 9/0014; A61K 9/0048; A61K 9/06; A61K 9/107; A61K 31/65; A61K 45/06; A61K 47/06; A61K 47/10; A61K 47/14; A61K 47/183; A61K 47/22; A61K 47/24; A61K 47/26; A61K 47/34; A61K 47/44
USPC ........................................................ 514/30
See application file for complete search history.

(56) References Cited

U.S. PATENT DOCUMENTS

| | | |
|---|---|---|
| 3,781,355 A | 12/1973 | Harrison et al. |
| 3,864,497 A | 2/1975 | Harrison et al. |
| 4,389,397 A | 6/1983 | Lo et al. |
| 4,957,918 A | 9/1990 | Martin et al. |
| 5,019,392 A | 5/1991 | Wallach |
| 5,338,533 A | 8/1994 | Derrieu |
| 5,614,545 A | 3/1997 | Martin et al. |
| 5,632,999 A | 5/1997 | Miller |
| 5,747,057 A | 5/1998 | Miller |
| 5,776,481 A | 7/1998 | Karst et al. |
| 5,952,372 A | 9/1999 | McDaniel |
| 5,968,990 A | 10/1999 | Jon et al. |
| 5,981,500 A | 11/1999 | Bishop et al. |
| 6,001,822 A | 12/1999 | Wicks et al. |
| 6,063,394 A | 5/2000 | Grosse-Bley et al. |
| 6,255,350 B1 | 7/2001 | Jon et al. |
| 6,500,446 B1 | 12/2002 | Derrieu et al. |
| 6,797,701 B2 | 9/2004 | Lukas et al. |
| 6,881,726 B2 | 4/2005 | Chang et al. |
| 7,064,108 B2 | 6/2006 | Guzzo et al. |
| 7,348,317 B2 | 3/2008 | Chang et al. |
| 7,531,186 B2 | 5/2009 | Boeckh et al. |
| 7,662,972 B2 | 2/2010 | Mita et al. |
| 7,906,128 B2 | 3/2011 | Heaney et al. |
| 7,906,130 B2 | 3/2011 | Sabnis et al. |
| 7,964,204 B2 | 6/2011 | Lahm et al. |

(Continued)

FOREIGN PATENT DOCUMENTS

| | | |
|---|---|---|
| CN | 102260252 | 11/2011 |
| CN | 102552114 A | 7/2012 |

(Continued)

OTHER PUBLICATIONS

Abd et al., "Minoxidil Skin Delivery from Nanoemulsion Formulations Containing Eucalyptol or Oleic Acid: Enhanced Diffusivity and Follicular Targeting", Pharmaceutics 2018; 10(19) in 12 pages.
Abelson et al., "Demystifying Dumulcents: A look at the varieties of this common agent and how they can help soothe patients' eyes." Review of Ophthalmology 2006: pp. 1-7.
Abelson et al., "Staying Local with Blepharitis Treatment", Review of Ophthalmology, Oct. 2012, pp. 60-62.
Aldrich et al., "Ophthalmic Preparations", Stimuli to the Revision Process, 2013, 39(5): in 21 pages.

(Continued)

*Primary Examiner* — Yih-Horng Shiao
(74) *Attorney, Agent, or Firm* — Knobbe Martens Olson & Bear LLP

(57) ABSTRACT

Formulation of ectoparasiticidal and antibiotic "compositions into pharmaceutical compositions useful for the treatment of eyelid inflammation, in particular demodex related blepharitis and eye crusting.

7 Claims, No Drawings

(56) References Cited

U.S. PATENT DOCUMENTS

| | | |
|---|---|---|
| 8,022,089 B2 | 9/2011 | Mita et al. |
| 8,128,968 B2 | 3/2012 | Gao et al. |
| 8,138,213 B2 | 3/2012 | Mita et al. |
| 8,207,206 B2 | 6/2012 | Nicoletti et al. |
| 8,231,888 B2 | 7/2012 | Lahm et al. |
| 8,242,161 B2 | 8/2012 | Boeckh et al. |
| 8,361,974 B2 | 1/2013 | Kaoukhov et al. |
| 8,362,069 B2 | 1/2013 | Diaz-Astruc et al. |
| 8,383,659 B2 | 2/2013 | Nanchen et al. |
| 8,389,738 B2 | 3/2013 | Kousaka et al. |
| 8,450,357 B2 | 5/2013 | Soll et al. |
| 8,455,015 B2 | 6/2013 | Gao et al. |
| 8,466,115 B2 | 6/2013 | Curtis et al. |
| 8,492,311 B2 | 7/2013 | Mita et al. |
| 8,501,799 B2 | 8/2013 | Derrieu |
| 8,541,413 B2 | 9/2013 | Wong et al. |
| 8,552,218 B2 | 10/2013 | Lahm et al. |
| 8,653,116 B2 | 2/2014 | Nanchen et al. |
| 8,790,674 B2 | 7/2014 | Derrieu et al. |
| 8,796,464 B2 | 8/2014 | Moriyama et al. |
| 8,815,816 B2 | 8/2014 | Manetta et al. |
| 8,871,941 B2 | 10/2014 | Lahm et al. |
| 8,921,408 B2 | 12/2014 | Soll et al. |
| 8,946,492 B2 | 2/2015 | Mita et al. |
| 8,987,218 B2 | 3/2015 | Kaoukhov et al. |
| 9,044,389 B2 | 6/2015 | Nanchen et al. |
| 9,066,515 B2 | 6/2015 | Boeckh et al. |
| 9,089,587 B2 | 7/2015 | Jacovella et al. |
| 9,095,566 B1 | 8/2015 | Yavitz et al. |
| 9,107,812 B2 | 8/2015 | Derrieu |
| 9,131,689 B2 | 9/2015 | Derrieu et al. |
| 9,173,728 B2 | 11/2015 | Wurtz |
| 9,173,870 B2 | 11/2015 | Fuchs et al. |
| 9,186,345 B2 | 11/2015 | Snorrason |
| 9,200,003 B2 | 12/2015 | Billen et al. |
| 9,233,117 B2 | 1/2016 | Jacovella et al. |
| 9,233,118 B2 | 1/2016 | Jacovella et al. |
| 9,260,231 B2 | 2/2016 | Havrileck et al. |
| 9,457,038 B2 | 10/2016 | Kaoukhov et al. |
| 9,532,978 B2 | 1/2017 | Fuchs et al. |
| 9,730,919 B2 | 8/2017 | Snorrason |
| 9,758,491 B2 | 9/2017 | Crouse et al. |
| 9,788,994 B2 | 10/2017 | Nichamin |
| 10,588,915 B2 | 3/2020 | Alster et al. |
| 10,688,122 B2 | 6/2020 | Amselem et al. |
| 10,835,517 B2 | 11/2020 | Borak |
| 11,197,847 B2 | 12/2021 | Azamian et al. |
| 11,690,826 B2 | 7/2023 | Azamian et al. |
| 11,690,827 B2 | 7/2023 | Azamian et al. |
| 11,752,137 B2 | 9/2023 | Azamian et al. |
| 2003/0059382 A1 | 3/2003 | Brandt |
| 2003/0181354 A1 | 9/2003 | Abdulrazik |
| 2004/0167084 A1 | 8/2004 | Parks |
| 2006/0154901 A1 | 7/2006 | Pflugfelder et al. |
| 2008/0039519 A1 | 2/2008 | Heine |
| 2008/0089958 A1 | 4/2008 | Diehl et al. |
| 2009/0093421 A1 | 4/2009 | Kaoukhov et al. |
| 2009/0317503 A1 | 12/2009 | Adkins, Jr. |
| 2010/0266628 A1 | 10/2010 | Razzak et al. |
| 2010/0273870 A1 | 10/2010 | Gao et al. |
| 2011/0033395 A1* | 2/2011 | Kaoukhov ............. A61P 31/00 424/59 |
| 2011/0059925 A1 | 3/2011 | Donnenfeld |
| 2011/0217249 A1 | 9/2011 | Dreher |
| 2011/0274631 A1 | 11/2011 | Kaoukhov et al. |
| 2012/0053140 A1 | 3/2012 | Kaoukhov et al. |
| 2013/0023490 A1 | 1/2013 | Boeckh et al. |
| 2013/0053374 A1 | 2/2013 | Inoue et al. |
| 2013/0101655 A1 | 4/2013 | Storm et al. |
| 2013/0317503 A1 | 11/2013 | Songer et al. |
| 2013/0324538 A1 | 12/2013 | Gauvry et al. |
| 2013/0344128 A1 | 12/2013 | Gao et al. |
| 2015/0086596 A1 | 3/2015 | Spallitta |
| 2016/0243116 A1 | 8/2016 | Jain |
| 2016/0256442 A1 | 9/2016 | Cady et al. |
| 2016/0287566 A1 | 10/2016 | Busby |
| 2016/0317439 A1 | 11/2016 | Lehay et al. |
| 2017/0020849 A1 | 1/2017 | Soll et al. |
| 2017/0024748 A1 | 1/2017 | Halder |
| 2017/0065565 A1 | 3/2017 | Mita et al. |
| 2017/0135978 A1 | 5/2017 | Spallitta |
| 2017/0196928 A1 | 7/2017 | McAnnally et al. |
| 2017/0232024 A1 | 8/2017 | Tan et al. |
| 2017/0239218 A1 | 8/2017 | Le Hir de Fallois et al. |
| 2017/0311601 A1 | 11/2017 | Yang et al. |
| 2020/0031859 A1 | 1/2020 | Santos et al. |
| 2020/0338105 A1 | 10/2020 | Tan et al. |
| 2021/0077465 A1 | 3/2021 | Azamian et al. |
| 2021/0077466 A1 | 3/2021 | Azamian et al. |
| 2021/0220360 A1 | 7/2021 | Kolhe |
| 2022/0160682 A1 | 5/2022 | Azamian et al. |
| 2022/0249445 A1 | 8/2022 | Azamian et al. |
| 2023/0190711 A1 | 6/2023 | Azamian et al. |
| 2023/0218584 A1 | 7/2023 | Azamian et al. |
| 2023/0293496 A1 | 9/2023 | Azamian et al. |
| 2023/0301971 A1 | 9/2023 | Azamian et al. |

FOREIGN PATENT DOCUMENTS

| | | |
|---|---|---|
| CN | 103687594 | 3/2014 |
| EP | 2 379 537 | 10/2012 |
| JP | 5246182 | 7/2013 |
| RU | 2126668 C1 | 7/2012 |
| RU | 2472505 | 1/2013 |
| RU | 2017100031 | 8/2018 |
| WO | WO 94/015597 | 7/1994 |
| WO | WO 99/058131 | 11/1999 |
| WO | WO 04/093886 | 11/2004 |
| WO | WO 06/050837 | 5/2006 |
| WO | WO 09/024541 | 2/2009 |
| WO | WO 13/039948 | 3/2013 |
| WO | WO 16/014664 | 1/2016 |
| WO | WO 16/022066 | 2/2016 |
| WO | WO 16/073347 | 5/2016 |
| WO | WO 16/102437 | 6/2016 |
| WO | WO 2016/207234 | 12/2016 |
| WO | WO 2017/147352 | 8/2017 |
| WO | WO 2017/178416 | 10/2017 |
| WO | WO 18/081733 | 5/2018 |
| WO | WO 19/126541 | 6/2019 |
| WO | WO 20/257663 | 12/2020 |
| WO | WO 2021/013825 | 1/2021 |
| WO | WO 21/041773 | 3/2021 |
| WO | WO 21/243014 | 12/2021 |

OTHER PUBLICATIONS

Ali et al., "Therapeutic efficacy of poly (lactic-co-glycolic acid) nanoparticles encapsulated ivermectin (nano-ivermectin} against brugian filariasis in experimental rodent model." Parasitol Res. Feb. 2014; 113(2):681-691: Abstract in 2 pages.

Allen, 2016, Ophthalmic preparations, Part 1: Ophthalmic solutions, International Journal of Pharmaceutical Compounding, 20:399-404.

Allergan, Inc. "Restasis® (cyclosporine ophthalmic emulsion)", Product Description; Dec. 2009 In 7 pages.

Almasieh et al., "Structural and functional neuroprotection in glaucoma: role of galantamine-mediated activation of muscarinic acetylcholine receptors", Cell Death and Disease (2010) 1, e27; doi:10.1038/cddis.2009.23: pp. 1-11.

Alphabetic List of all veterinary anti-helminthics—Parasiteopedia Jul. 2017, in 2 pages.

American Academy of Ophthalmology [AAO] Cornea/External Disease Panel. Preferred Practice Pattern® Guidelines. Blepharitis. San Francisco, CA: American Academy of Ophthalmology; 2013. Available at: www.aao.org/ppp in 31 pages.

American Academy of Ophthalmology [AAO] Cornea/External Disease Panel. Preferred Practice Pattern® Guidelines. Blepharitis. San Francisco, CA: American Academy of Ophthalmology: 2018. Available at: www.aao.org/ppp in 38 pages.

(56) References Cited

OTHER PUBLICATIONS

Ames et al., "Cyclosporine ophthalmic emulsions for the treatment of dry eye: a review of the clinical evidence", Clin Investig (Lond). 2015, 5(3):267-285,.
Anadón et al., "Use and abuse of pyrethrins and synthetic pyrethroids in veterinary medicine", The Vet J. 2009, 182:7-20.
Animalytix LLC. "Bimectin®—Injection for Cattle & Swine", Bimedia Inc., 2016: in 5 pages.
Anonymous (2014). "Safety Assessment of Tocopherols and Tocotrienols as Used in Cosmetics,"Cosmetics Ingredient Review, Washington, DC, 36 total pages.
Anonymous (1984). "Final Report on the Safety Assessment of Fossil and Synthetic Waxes," International Journal of Toxicology 3:43-99.
Anonymous (1992). "Final Report on the Safety Assessment of Methylisothiazolinone and Methylchloroisothiazlinone," Journal of the American College of Toxicology 11 :75-128.
Anonymous (2002). "Final Report on the Safety Assessment of EDTA, calcium disodium EDTA,diammonium EDTA, dipotassium EDTA, disodium EDTA, TEA-EDTA, tetrasodium EDTA, tripotassiumEDTA, trisodium EDTA, HEDTA, and trisodium HEDTA," International Journal of Toxicology 21(Suppl. 2):95-142.
Anonymous (2013). "Amended Safety Assessment of Alkyl Esters as Used in Cosmetics," Cosmeticsingredient Review, Washington, DC, 82 total pages.
Armstrong Rob., "The conclusion of a comparative efficacy study of fluralaner and sarolaner against the tick *Amblyomma americanum* on dogs is based on results obtained at study times that are outside the fluralaner label recommendations", Parasit Vectors. 2017, 10:159 in 2 pages.
Arrúa et al., "Comparative study of the efficacy of different treatment options in patients with chronic blepharitis", Arch Soc Esp Oftalmol. 2015, 90(3):112-118.
Asahi et al., "Differential mechanisms of action of the novel γ-aminobutyric acid receptor antagonist ectoparasiticides fluralaner (A1443) and fipronil", Pest Manag Sci. 2015, 71:91-95; Epub Mar. 31, 2014.
Asahi et al., Feb. 5, 2018, Fluxametamide: A novel isoxazoline insecticide that acts via distinctive antagonism of insect ligand-gated chloride channels, Pesticide Biochemistry and Physiology (2018). https://dot.org/10.1016/j.pestbp.2018.02.2002; Elsevier Inc.
Asbell et al., "The International Workshop on Meibomian Gland Dysfunction: Report of the Clinical Trials Subcommittee", IOVS, Special Issue 2011, 52(4):2065-2085.
Asoklis et al., "Ocular Rosacea", N Engl J Med. 2016, 374(8):771.
Australian Pesticides & Veterinary Medicines Authority; "Pastoral Ag Fluazuron pour-on tick development inhibitor for cattle", Application Summary for Application No. 104014, 2015, in 5 pages.
Australian Pesticides and Veterinary Medicines Authority [APVMA], "Safety of Fipronil in Dogs and Cats: A review of literature", 2011, pp. 1-21.
Avdeef Alex, "Solubility Temperature Dependence Predicted from 2D Structure", ADMET & DMPK2015, 3(4):298-344.
Ayres et al., "Acne Rosacea Response to Local Treatment for Demodex Folliculorium", JAMA. 1933, 100(9):645-647.
Bahmani et al., "Comparison of effect of nicotine and levamisole and ivermectin on mortality of leech", Asian Pac J Trop Dis. 2014, 4(Suppl 1):S477-S480.
Baranowski et al., "Ophthalmic Drug Dosage Forms: Characterization and Research Methods", ScientificWorldJournal, 2014, Article ID 861904 in 15 pages.
Barnhorst et al., "The Efficacy of Topical Metronidazole in the Treatment of Ocular Rosacea", Ophthalmology 1996; 103:1880-1883.
Becskei et al., "Comparative speed of kill of oral treatments with Simparica™(sarolaner) and Bravecto®(fluralaner) against induced infestations of hipicephalus sanguineus on dogs", Parasit Vectors. 2016: pp. 1-6.
Bernigaud et al. "Efficacy and Pharmacokinetics Evaluation of a Single Oral Dose of Afoxolaner against Sarcoptes scabiei in the Porcine Scabies Model for Human Infestation", Antimicrob Agents Chemother. 2018, 62(9):e02334-17 in 12 pages.
Beugnet et al., "Comparative efficacy of two oral treatments for dogs containing either afoxolaner or fluralaner against Rhipicephalus sanguineus sensu lato and Dermacentor reticulatus" Veterinary Parasitology 209 (2015): pp. 142-145.
Beugnet et al., "Comparative speed of efficacy against Ctenocephalides felis oftwo oral treatments for dogs containing either afoxolaner orfluralaner", Vet Parasitol. 2015, 207: pp. 297-301.
Beugnet et al., "Insecticide and acaricide molecules and/or combinations to prevent pet infestation by ectoparasites", Trends Parasitol. 2012, 28(7):267-279.
Bezerra Da Silva et al., "Effect of Donepezil, Tacrine, Galantamine and Rivastigmine on Acetylcholinesterase Inhibition in Dugesia tigrina" Molecules 2016, 21, 53:1-11.
Biernat et al., "Occurrence of Demodex species in patients with blepharitis and in healthy individuals: a 10-year observational study", Japanese Ophthalmological Society, Sep. 2018, 62:628-633.
Bimeda, "Bimectin Pour-On (Ivermectin Pour-On)", Safety Data Sheet, 2015, 77(58): in 8 pages.
Bos et al., "The 500 Dalton rule for the skin penetration of chemical compounds and drugs", Exp Dermatol. 2000, 9:165-169.
Brayden et al., "Drug Delivery Systems in Domestic Animal Species", in Handbook of Experimental Pharmacology by F. Cunningham et al. (eds.), 2010; (199):79-112.
Brimecombe et al., "Electrochemical investigation of the effect of pH and solvent on amitraz stability." J Agric Food Chem. Oct. 18, 2006, 54(21):8139-8143; Abstract in 2 pages.
Bron Anthony, "Ocular rosacea", UpToDate 2016 (www.uptodate.com), Wolters Kluwer in 24 pages.
Brown, M. et al. (2014). "Severe demodexfolliculorum-associated oculocutaneous rosacea in a girlsuccessfully treated with ivermectin," JAMA Dermatol. 150:61-63.
Burgio et al., "A comparative laboratory trial evaluating the immediate efficacy of fluralaner, afoxolaner, sarolaner and imidacloprid + permethrin against adult *Rhipicephalus sanguineus* (sensu lato) ticks attached to dogs", Parasit Vectors. 2016, 9:626 in 6 pages.
CAMPBELL William C., "Ivermectin as an Antiparasitic Agent for Use in Humans", Annu Rev Microbial. 1991, 45:445-474.
Cardwell et al., "New developments in the treatment of rosacea—role of once-daily ivermectin cream", Clin Cosmetic Invest Dermatol. 2016, 100(9):71-77.
Carson et al., "*Melaleuca alternifolia* (Tea Tree) Oil: a Review of Antimicrobial and Other Medicinal Properties" Clin Microbiol Rev. 2006, 19(1):50-62.
Casida et al., "Novel GABA receptor pesticide targets", Pest Biochem Physiol. Jun. 2015, (121):22-30.
Casida, "Golden Age of RyR and GABA-R Diamide and Isoxazoline Insecticides: Common Genesis, Serendipity, Surprises, Selectivity, and Safety", Chem Res Toxicol. 2015; 28:560-566.
Casida, "Radioligand Recognition of Insecticide Targets" J. Agric. Food Chem. 2018, 66: pp. 3277-3290.
Cavalleri et al., "A randomised, blinded, controlled field study to assess the efficacy and safety of lotilaner tablets (Credelio™) in controlling fleas in client-owned dogs in European countries" Parasit Vectors. 2017, 10:526 in 8 pages.
Cavalleri et al., "A randomized, controlled study to assess the efficacy and safety of lotilaner (Credelio™) in controlling ticks in client-owned dogs in Europe" Parasit Vectors. 2017, 10:531 in 8 pages.
Cavalleri et al., "Assessment of the onset of lotilaner (Credelio™) speed of kill of fleas on dogs" Parasit Vectors (2017) 10:521 in 5 pages.
Cavalleri et al., "Assessment of the speed of flea kill of lotilaner (Credelio™) throughout the month following oral administration to dogs", Parasit Vectors (2017) 10:529 in 8 pages.
Cavalleri et al., "Laboratory evaluations of the immediate and sustained effectiveness of lotilaner (Credelio™) against three common species of ticks affecting dogs in Europe" Parasit Vectors. 2017, 10:527 in 7 pages.
Cavalleri et al., "Two randomized, controlled studies to assess the efficacy and safety of lotilaner (Credello™) in preventing *Dermacen-*

(56) References Cited

OTHER PUBLICATIONS

*tor reticulatus* transmission of *Babesia canis* to dogs", Parasit Vectors. 2017, 10:520 in 7 pages.
Chavez Fernando, "Case Report of Afoxolaner Treatment for Canine Demodicosis in Four Dogs Naturally Infected with Demodex Canis" Intern J Appl Res Vet Med 2016, 14(2):123-127.
Chen et al., "Human demodicosis: revisit and a proposed classification", Br J Dermatol. 2014, 170:1219-1225.
Cheng et al. Current Opinion in Ophthalmology (2015), vol. 26(4), pp. 295-300 (Year: 2015).
Cheung et al., "In vitro anti-demodectic effects and terpinen-4-ol content of commercial eyelid cleansers", Contact Lens Anterior Eye. 2018, 41:513-517.
Chiodini et al., "Parenteral ivermectin in Strongyloides hyperinfection", The Lancet. 2000, 335:43-44.
Clark et al., "Long-term delivery of ivermectin by use of poly(D,L-lactic-co-glycolic)acid microparticles in dogs", AJVR, 2004, 65(6):752-757.
Cliradex® Blepharitis Kit, available at https://cliradex.com/product/cliradex-blepharitis-kit/ (accessed Apr. 4, 2022) 6 pp.
Cliradex® Towelettes Patient Brochure, CX-003 Rev D, Mar. 9, 2016, available at https://cliradex.com/wp-content/uploads/2019/12/cliradex-instructions-for-use.pdf (accessed Apr. 4, 2022) 1 p.
Čolović et al., "Acetylcholinesterase Inhibitors: Pharmacology and Toxicology" Current Neuropharmacology, 2013, 11(3):315-335.
Corta et al., "Kinetics and mechanism of amitraz hydrolysis in aqueous media by HPLC and GC-MS." Talanta. 1999, 48(1):189-99; Abstract in 1 page.
Cosmetic Ingredient Report Expert Panel Meeting (2010). Cosmetic Ingredient Review, 29 totalpages.
Costa et al., "Alpha 2-adrenoceptors as a target for formamidine pesticides: in vitro and in vivo studies in mice." Toxicol Appl Pharmacol. 1988, 93(2):319-28, Abstract in 2 pages.
Costa et al., "Ivermectin for spasticity in spinal-cord injury" The Lancet 1994, 343:739.
Cresswell James E., "A meta-analysis of experiments testing the effects of a neonicotinoid Insecticide (imidacloprid) on honey bees", Ecotoxicology Nov. 16, 2010 in 9 pages.
Crosaz et al., "Open field study on the efficacy of oral fluralaner for long-term control of flea allergy dermatitis in client-owned dogs in Ile-de-France region", Parasit Vectors.. 2016, 9:174 in 5 pages.
Dadzie et al., "Ocular findings in a double-blind study of ivermectin versus diethylcarbamazine versus placebo in the treatment of onchocerciasis", Br J Ophthalmol. 1987, 71:78-85.
De Oliveira et al., "Toxicity effect of the acaricide fipronil in semi-engorged females of the tick *Rhipicephalus sanguineus* (Latreille, 1806) (Acari: Ixodidae): Preliminary determination of the minimum lethal concentration and LC50", Exper Parasitol. 2011, 127:418-422.
De Sole et al., "Adverse reactions after large-scale treatment of onchocerciasis with ivermectin: combined results from eight community trials", WHO Bulletin, 1989, 67(6):707-719.
De Sole et al., "Lack of adverse reactions in ivermectin treatment of onchocerciasis" The Lancet, 1990, 335:1106-1107.
Del Pino et al., "Molecular Mechanisms of Amitraz Mammalian Toxicity: A Comprehensive Review of Existing Data" Chem. Res. Toxicol. 2015, 28:1073-1094.
Do, et al., Setting of ADI for MRLs establishment of insecticide fluxametamide, URL: http://www.dbpia.co.kr/Article/NODE027269043; The 59th Biannual Conference of the Korean Society of Analytical Sciences, Nov. 2017, p. 154 (1 page).
Doan et al., "The efficacy of avermectins (ivermectin, doramectin and abamectin) as treatments for infestation with the tick *Haemaphysalis longicornis* on rabbits in Korea", Vet Parasitol. 2013, 198:406-409.
Dorati et al., "Stability Evaluation of Ivermectin-Loaded Biodegradable Microspheres", AAPS PharmSciTech, 2015, 16(5):1129-1139.
Doshi et al., "Effect of Viscosity, Surface Tension and Mucoadhesion on Ocular Residence Time of Lubricant Eye Drops" Invest Ophthal Visual Science. Apr. 2009, 50:4641; ARVO Annual Meeting Abstract in 2 pages.
Dourmishev et al., "Ivermectin: pharmacology and application in dermatology", Intern J Dermatol. 2005, 44:981-988.
Drugbank, "Levamisole"—Accession No. DB00848 (APRD01067)—DrugBank, 2017, in 10 pages.
Drugs.com, "Ivermectin", Monograph for Professionals, Am Society of Health-Sys Pharmacists, Inc. [AHFS DI Essentials] 2013, in 19 pages.
Drugs.com, "Metronidazole", Monograph for Professionals, Am Society of Health-Sys Pharmacists, Inc. [AHFS] 2007 in 36 pages.
Dryden et al., "Evaluation of fluralaner and afoxolaner treatments to control flea populations, reduce pruritus and minimize dermatologic lesions in naturally infested dogs in private residences in west central Florida USA", Parasit Vectors. 2016, 9:365 in 11 pages.
Dryden et al., "Efficacy of fluralaner flavored chews (Bravecto®) administered to dogs against the adult cat flea, Ctenocephalides felis felis and egg production", Parasit Vectors.. 2015, 8:364 in 7 pages.
Durvet, "Ivermectin Injection", Bimeda-MTC Animal Health Inc., Material Safety Data Sheet, ANADA 200-447, 2011, in 6 pages.
Durvet, "Ivermectin Sheep Drench", Material Safety Data Sheet, First Priority Inc. Jun. 2, 2002,in 3 pages.
Egeberg et al., "Patients with Rosacea Have Increased Risk of Dementia", Ann Neurol. 2016, 79(6):921-928.0.
Eizadi-Mood et al., "Amitraz Poisoning Treatment: Still Supportive?" Iranian J Pharma Res. 2011, 10(1):155-158.
Elston, "Demodex mites: facts and controversies." Clin Dermatol 2010; 28(5):502-504 [Abstract].
Environmental Protection Agency [EPA], Amitraz R.E.D. Facts Sheet EPA-738-F-96-031, 1996, in 11 pages.
Environmental Protection Agency [EPA], "Carbaryl" Summary (1992): pp. 1-4.
Environmental Protection Agency [EPA], "Fipronil—Environmental Impact Summary for DP Barcode D338854", (2007): pp. 1-71.
Environmental Protection Agency [EPA], Fipronil—New Pesticide Fact Sheet CAS #120068-37-3; (1996): pp. 1-10.
Environmental Protection Agency [EPA], "Margosan-O", Azadirachtin Summary and Registration for Vikwood Ltd. (1984): pp. 1-11.
Erdemir et al., "Demodex mites in acne rosacea: reflectance confocal microscopic study", Australas J Dermatol. 2017, 58(2):e26-e30.
Estermann et al., "Effect of Oral Donepezil on Intraocular Pressure in Normotensive Alzheimer Patients" J Ocular Phama Thera. 2006, 22(1):62-67.
Ethiopia Sheep and Goat Productivity Improvement Program (ESGPIP), "Control of External Parasites of Sheep and Goats" Technical Bulletin No. 41 , 2010: pp. 1-16.
European Medicines Agency [EMA]—Committee for Human Medicinal Products (CHMP/463/00 Rev.1), "Background review for the excipient propylene glycol", Summary of Propylene Glycol Excipient, EMA. Nov. 2014, in 96 pages.
European Medicines Agency [EMA]—Veterinary Medicines and Inspections: "Fluazuron—Summary Report", European Medicines Agency: EMEA/CVMP/77290/05-Final; 2005 in 5 pages.
European Medicines Agency [EMA]—Veterinary Medicines Division, "CVMP assessment report for Bravecto for spot-on solution for dogs and cats (EMEA/V/C/002526/X/0005)"; Mar. 18, 2016: pp. 1-34.
European Medicines Agency [EMA], "European public MRL assessment report (EPMAR)—Fluralaner (poultry)", Feb. 15, 2017: pp. 1-12.
European Medicines Agency [EMA]—Veterinary Medicines Division, "CVMP Assessment Report for NexGard", Committee for Medicinal Products for Veterinary Use (CVMP), Dec. 12, 2013, in 21 pages.
European Medicines Agency [EMA]—Veterinary Medicines Division, "CVMP Assessment Report for SIMPARICA", Committee for Medicinal Products for Veterinary Use (CVMP), Sep. 10, 2015, in 26 pages.

(56) References Cited

OTHER PUBLICATIONS

European Medicines Agency [EMA]—Veterinary Medicines Evaluation Unit, "Cymiazole", Committee for Veterinary Medical Products, Summary Report, Mar. 1996 in 7 pages.
European Union [EU], "Directive 98/8/EC concerning the placing of biocidal products on the market—Imidacloprid", Assessment Report, Feb. 18, 2011, in 131 pages.
Farkouh et al., "Systemic side effects of eye drops: a pharmacokinetic perspective" Clin Ophthalmol. 2016, 10:2433-2441.
FDA Center for Veterinary Medicine, "Animal Drug Safety Communication: FDA Alerts Pet Owners and Veterinarians About Potential for Neurologic Adverse Events Associated with Certain Flea and Tick Products" dated Aug. 5, 2019 and updated Apr. 22, 2019; https://www.fda.gov/animal-veterinary/cvm-updates/animal-drug-safety-communication-fda-alerts-pet-owners-and-veterinarians-about-potential-neurologic (3 pages).
Federal Drug Administration [FDA], "Afoxolaner, Fluralaner and Sarolaner", FDA-CVM FOIA Response 2017-963: pp. 1-26.
Filho et al., "The efficacy of oral ivermectin for the treatment of chronic blepharitis in patients tested positive for *Demodex* spp.". Br J Ophthamol. Jun. 2011, 95(6): 893-895.
Fisara et al., "A randomized controlled trial of the efficacy of orally administered fluralaner (Bravecto™) against induced Ixodes holocyclus (Australian paralysis tick) infestations on dogs", Parasit Vectors.. 2015, 8:257 in 6 pages.
Fisara et al., "A small-scale open-label study of the treatment of canine flea allergy dermatitis with fluralaner", Vet Dermatol. 2015, 26: pp. 417-e98.
Flajs et al., "Ivermectin Pharmacokinetics", Slov Vet Res 2002; 39(3/4):167-178.
Fluralaner—Bravecto—for veterinary use in Dogs and Cats against fleas and ticks (Jul. 11, 2017), Retreived from: http://parasilipedia.net/index.php?option=com_content&view=article&id=2731&Itemid=2955, in 3 pages.
Folz et al., "Clinical evaluation of Amitraz as a treatment for canine demodicosis" Vet Parasit. 1984, 16:335-341.
Folz et al., "Evaluation of a topical treatment, alone and in combination with a detergent, for generalized demodicosis" Vet Parasitol., 1984/85, 17:165-172.
Food & Drug Administration [FDA] Veterinary Freedom of Information Summary "Nexgard—Afoxolaner", 2013, in 22 pages.
Food & Drug Administration [FDA], "21-169_Reminyl_medr_P4", 2001, Part 4, Medical Review, retrieved from URL: <https://www.accessdata.fda.gov/drugsatfda_docs/nda/2001/21-169_Remiryl_medr_P4.
Food And Drug Administration [FDA], "Bravecto", Freedom of Information Summary NADA 141-426, May 15, 2014; in 39 pages.
Food And Drug Administration [FDA], CFR 21, vol. 5, Part 349 "Ophthalmic Drug Products for over-the-counter human use", [Revised as of Apr. 1, 2016] in 9 pages.
Forton et al., "Demodex folliculorum and topical treatment: acaricidal action evaluated by standardized skin surface biopsy.", Br J Dematol. Mar. 1998, 138(3):461-466 [Abstract].
Foulks et al., [Eds.], "Special Issue—International Dry Eye WorkShop (DEWS) Report", The Ocular Surface, Apr. 2007, 5(2):59-142.
Fourie et al., "Efficacy of a novel formulation of metaflumizone plus amitraz for the treatment of sarcoptic mange in dogs" Vet Parasitol. 2007, 150:275-281.
Fourie et al., "Efficacy of a topical application of Certifect (fipronil 6.26% w/v, amitraz 7.48% w/v, (S)-methoprene 5.63% w/v) for the treatment of canine generalized demodicosis" Parasite 2013, 20:46 in 6 pages.
Fourie et al., "Efficacy of orally administered fluralaner (Bravecto™) or topically applied imidacloprid/moxidectin (Advocate®) against generalized demodicosis in dogs" Fourie et al. Parasit Vectors., 2015, 8:187 in 7 pages.
Frame et al., "Comparing the in vitro effects of MGO™ Manuka honey and tea tree oil on ocular *Demodex* viability" Contact Lens Anterior Eye 2018, 41(6):527-530.

Galderma Laboratories, LP., "Soolantra™ (ivermectin) cream", Highlights of Prescribtion Information: Dec. 2014, in 8 pages.
Gao et al., "Clinical Treatment of Ocular Demodecosis by Lid Scrub With Tea Tree Oil", Cornea, Mar. 2007, 26:136-143.
Gao et al., "High Prevalence of Demodex in Eyelashes with Cylindrical Dandruff" Invest Ophthalmol Vis Sci. 2005; 46(9):3089-3094.
Gao et al., "In vitro and in vivo killing of ocular Demodex by tea tree oil" Br J Ophthalmol 2005; 89:1468-1473.
Gardon et al., "Serious reactions after mass treatment of onchocerciasis with ivermectin in an area endemic for Loa loa infection" The Lancet, 1997, 350:18-22.
Gassel et al., "The novel isoxazoline exctoparasiticide fluralaner: Selective inhibition of arthropod γ-aminobutyric acid- and L-glutamate-gated chloride channels and insecticidal/ acaricidal activity", Insect Biochem Mol Biol. 2014; 45:111-124.
Geerling et al., "The International Workshop on Meibomian Gland Dysfunction: Report of the Subcommittee on Management and Treatment of Meibomian Gland Dysfunction", IOVS, Special Issue 2011, 52(4):2050-2064.
Gibbons et al., "A review of the direct and indirect effects of neonicotinoids and fipronil on vertebrate wildlife", Environ Sci Pollut Res. 2015, 22:103-118.
Gonzalez-Salinas et al., Sep. 21, 2021, Safety and efficacy of topical lolitaner ophthalmic solution 0.25% for the treatement of demodex blepharitis: a pilot study, Journal of Ophthalmology, 2021:1-7.
Gordon D.M., "Dimethyl Sulfoxide in Ophthalmology, with Especial Reference to Possible Toxic Effects", Biol Actions of Dimethyl Sulfoxide, 1967, 141:392 in 4 pages.
Government Publishing Office, "Ophthalmic and Topical Dosage Form New Animal Drugs; Ivermectin Topical Solution", 21 CFR Part 524; FR 2011, 76(250):81806-7.
Green-Church et al., "The International Workshop on Meibomian Gland Dysfunction: Report of the Subcommittee on Tear Film Lipids and Lipid-Protein Interactions in Health and Disease" IOVS, Special Issue 2011, 52(4):1979-1993.
Grubbs Jr. et al., "Instrument Development of the UNC Dry Eye Management Scale", Cornea. Nov. 2014, 33(11):1186-1192.
Gupta et al., "Ivermectin 1% Cream for Rosacea", SkinTherapyLetter.com, Dec. 15, 2015, in 6 pages.
Gupta Ramesh C. [Ed.], "Amitraz", Vet Toxicol. 2007, Chapter 46, pp. 514-517.
Guzzo et al., "Safety, Tolerability, and Pharmacokinetics of Escalating High Doses of Ivermectin in Healthy Adult Subjects", J Clin Pharmacol. 2002, 42:1122-1133.
Hainzl et al., "Mechanisms for Selective Toxicity of Fipronil Insecticide and Its Sulfone Metabolite and Desulfinyl Photoproduct", Chem Res Toxicol. 1998, 11(12):1529-1535.
Halos et al., "Preference of Dogs between Two Commercially Available Oral Formulations of Ectoparasiticide Containing Isoxazolines, Afoxolaner or Fluralaner", Open J Vet Med. 2015, 5:25-29.
Herath et al., "Amitraz poisoning: A case report of an unusual pesticide poisoning in Sri Lanka and literature review" BMC Pharmacol Toxicol. (2017) 18(6):1-6.
Herrero, V.R., "Preservatives in Ophthalmic Formulations: An Overview", Arch Soc Esp Oftalmol. 2007; 82(9):531-532.
Holland et al., "Lifitegrast for the Teatment of Dry Eye Disease—Results of a Phase III Trial (OP3)", Ophthalmol. Jan. 2017, 124(1):53-60.
Holzchuh et al., "Clinical Treatment of Ocular *Demodex folliculorum* by Systemic Ivermectin" Am J Ophthalmol., 2011, 151:1030-1034.
Hom et al. Randomized Controlled Trial to Evaluate the Safety and Efficacy of TP-03 for the Treatment of Blepharitis Due to Demodex Infestation (Jupiter Study—Phase 2B—Presented at AOA 2020 Virtual Meeting Jun. 26, 2020 available at https://www.tarsusrx.com/jupiter-study (accessed Jul. 13, 2020) in 3 pages.
Hom et al., "Understanding Emulsion Eye Drop Technology", Rev Optometry. Mar. 2003, 140(3)in 6 pages.
Hosseini et al., "Development and evaluation of a measure of patient-reported symptoms of Blepharitis" Health and Quality of Life Outcomes, 2018, 16:11 in 6 pages.

(56) References Cited

OTHER PUBLICATIONS

Inceboz et al., "Diagnosis and Treatment of Demodecitic Blepharitis" Türkiye Parazitoloji Dergisi, 2009: 33 (1):p. 32-36.
Intervet Australia Pty Limited, "Bravecto Fluralaner Chewable Tablets for Dogs", Material Safety Data Sheet Feb. 2015, Version 1: pp. 1-11.
Ismailos et al., "Unusual solubility behaviour of cyclosporin A in aqueous media" J Pharm Pharmacol. 1991, 43:287-289.
Jackson Jeremy D., "Infectious folliculitis", UpToDate 2016 (www.uptodate.com) Wolters Kluwer. 2016, in 39 pages.
Jacobi et al., "Demodex Follicularum in dry eye patients" TFOS 2016 poster in 2 pages.
Jańczak et al., "Clinical aspects of demodicosis in veterinary and human medicine", Med Weter. 2017, 73(5):265-271.
Jarmuda, S. et al. (2012). "Potential role of *Demodex* mites and bacteria in the induction of rosacea,"J. Med. Microbial. 61 (Pt. 11):1504-1510.
Jarmuda, S. et al. (2014). "Correlation between serum reactivity to Demodex-associated Bacillusoleronius proteins, and altered sebum levels and Demodex populations in erythematotelangiectaticrosacea patients," J. Med. Microbial. 63(Pt. 2):258-262.
Jelic et al., "Donepezil: A Review of Pharmacological Characteristics and Role in the Management of Alzheimer Disease" Clin Med Insights: Therapeutics 2010, 2:771-788.
Jia et al., "Acute Toxicity, bioconcentration, elimination and antioxidant effects of fluralaner in zebrafish *Danio rerio*", Environ Pollut. 2018, 232:183-190; Epub Sep. 15, 2017.
Jiang et al., "Mosquitocidal Activity and Mode of Action of the Isoxazoline Fluralaner", Int J Environ Res Public Health. 2017, 14:154 in 17 pages.
Johnson, W. (2011). "Safety Assessment of Cyclomethicone, Cyclotetrasiloxane, Cyclopentasiloxane, Cyclohexasiloxane, and Cycloheptasiloxane," International Journal of Toxicology 30(Suppl. 3):149S-227S.
Jon et al., "Liquid matrices for insecticides for "pour on" applications in queous medium - Amitraz As A Case Study", in *Pesticide Formulations and Application Systems: Eighteenth Volume, ASTM STP 1347* [Nalewaja et al.—Eds.] 1998, pp. 228-241.
Jongejan et al., "Comparative efficacy of oral administrated afoxolaner (NexGard™) and fluralaner (Bravecto™) with topically applied permethrin/imidacloprid (Advantix®) against transmission of Ehrlichia canis by infected *Rhipicephalus sanguineus* ticks to dogs", Parasit Vectors. 2016, 9:348 in 14 pages.
Jonsson et al., "Critical evaluation of the modified-adult immersion test with discriminating dose bioassay for Boophilus microplus using American and Australian isolates" Vet Parasitol. 2007, 146:307-315.
Junquera P., "Fluralaner: Safety Summary for Veterinary use in Dogs & Cats (Bravecto)", 2017 in 3 pages.
Kabat Alan G., "In-Vitro Demodicidal Activity of Commercial Lid Hygiene Products" Southern College of Optometry. (2018) Poster in 1 page.
Kagaruki, "The efficacy of amitraz against cattle ticks in Tanzania" Onderstepoort J Vet Res. 1996, 63:91-96.
Karadzovska et al., "A randomized, controlled field study to assess the efficacy and safety of lotilaner flavored chewable tablets (Credelio™) in eliminating fleas in client-owned dogs in the USA", Parasit Vectors. 2017, 10:528 in 9 pages.
Kaushik et al., "Acetylcholinesterase Inhibitors: Beneficial Effects on Comorbidities in Patients With Alzheimer's Disease" Am J Alzheimers Dis Other Demen. 2018, 33(2):73-85; Epub Oct. 3, 2017 in 13 pages.
Kheirkhah et al., "Fluorescein Dye Improves Microscopic Evaluation and Counting of *Demodex* in Blepharitis With Cylindrical Dandruff" Cornea 2007;26:697-700.
Kilp et al., "Comparative pharmacokinetics of fluralaner in dogs and cats following single topical or intravenous administration", Parasit Vectors. 2016; 9(296) in 7 pages.
Kilp et al., "Pharmacokinetics of fluralaner in dogs following a single oral or intravenous administration" Parasit Vectors 2014, 7:85: pp. 1-5.
Kita et al., "Amitraz and its metabolite differentially activate α- and β-adrenergic-like octopamine receptors." Pest Manag Sci. 2017; 73(5):984-990, Abstract in 2 pages.
Kita et al., "Pharmacological characterization of histamine-gated chloride channels from the housefly *Musca domestica*", NeuroToxicology 60 (2017): pp. 245-253.
Knop et al., "The International Workshop on Meibomian Gland Dysfunction: Report of the Subcommittee on Anatomy, Physiology, and Pathophysiology of the Meibomian Gland", IOVS, Special Issue 2011, 52(4):1938-1978.
Kojima et al., "In Vivo Evaluation of Ocular Demodicosis Using Laser Scanning Confocal Microscopy", Invest Ophthalmol Visual Science. Jan. 2011, 52(1): 565-569.
Kong et al., "Absolute configuration assignment of (+)-fluralaner using vibrational circular dichroism" Chirality. 2017, 29:854-864.
Kong et al., "Solubility of Imidacloprid in Different Solvents", J Chem Eng Data, 2008, 53:615-618.
Koo et al., "Ocular Surface Discomfort and Demodex: Effect of Tea Tree Oil Eyelid Scrub in Demodex Blepharitis", J Korean Med Sci 2012; 27:1574-1579.
Kugadas et al., "Impact of Microbiome on Ocular Health", The Ocular Surface, Jul. 2016, 14(3):342-349.
Kuntz et al., "Safety evaluation of lotilaner in dogs after oral administration as flavoured chewable tablets (Credelio™)", Parasit Vectors. 2017, 10:538 in 6 pages.
Lacey et al., "*Demodex* Mites-Commensals, Parasites or Mutualistic Organisms?" Dermatology 2011; 222:128-130.
Lacey et al., "Mite-related bacterial antigens stimulate inflammatory cells in rosacea", Br J Dermatol. 2007, 157(3):474-481.8.
Lacey et al., "Study of *Demodex* mites: Challenges and Solutions" JEADV 2016, 30:764-775.
Lacey et al., "Under the lash: *Demodex* mites in human diseases" Biochem (Lond) 2009 31(4):2-6.
Laspina et al., "*Demodex* ssp en pacientes con blefaritis crónica", Rev Chilena Infectol 2015; 32(1):37-42.
Lemp et al., "Blepharitis in the United States 2009: A Survey-based Perspective on Prevalence and Treatment" The Ocular Surface, Apr. 2009, 7(2):S1-22.
Lexicomp, Inc. Ivermectin (systemic): Drug information, 2016, in 6 pages.
Li, J. et al. (2010). "Correlation between ocular Demodex infestation and serum immunoreactivity toBacillus proteins in patients with Facial rosacea," Ophthalmology 117:870-877.
Liang et al., "High Prevalence of *Demodex brevis* Infestation in Chalazia" Am J Ophthalmol 2014, 157:342-348.
Lifschitz et al., "Comparative distribution of ivermectin and doramectin to parasite location tissues in cattle", Vet Parasitol. 2000, 87:327-338.
Lilienfeld Sean, "Galantamine—a Novel Cholinergic Drug with a Unique Dual Mode of Action for the Treatment of Patients with Alzheimer's Disease" CNS Drug Reviews, 2002, 8(2): 159-176.
Lindsley et al., "Interventions for chronic blepharitis", Cochrane Database Syst Rev. Dec. 2014, 5:e in PMC Dec. 18, 2014, CD005556. doi:10.1002/14651858.CD005556.pub2; in 117 pages.
Little Susan E., "Lotilaner—a novel systemic tick and flea control product for dogs", Parasit Vectors. 2017, 10:539 in 3 pages.
Liu et al., "Pathogenic role of *Demodex* mites in blepharitis", Curr Opin Allergy Clin Immunol. Oct. 2010, 10(5):505-510.
Lu, G.W., "Recent advances in developing ophthalmic formulations: a patent review", Recent Pat Drug Deliv Formul. Jan. 2010, 4(1):49-57; Abstract in 1 page.
Luntz et al., "Azadirachtin from the Neem Tree *Azadirachta indica*: its Action Against Insects" An. Soc. Entomol. Brasil. 2000, 29(4):615-632.
Mabrouk ST. The Preparation and Testing of a Common Emulsion and Personal Care Product: Lotion. Journal of Chemical Education vol. 81, No. 1, p. 83-86, 2004. (Year: 2004).
Maier, "Management of rosacea" UpToDate 2016 (www.uptodate.com), Wolters Kluwer, in 28 pages.

(56) References Cited

OTHER PUBLICATIONS

Marie Miglianico, et al., Repurposing isoxazoline veterinary drugs for control of vector-borne human diseases; PNAS; vol. 115, No. 29, pp. E6920-E6926 (6 pages). URL: www.pnas.org/cgi/doi/10.1073/pnas.1801338115 (year 2018).
Marty et al., "Treatment of Human Disseminated Strongyloidiasis with a Parenteral Veterinary Formulation of Ivermectin", Clin Infect Diseases. 2005, 41: e5-8.
Matricoti et al., "The use of oral fluralaner for the treatment of feline generalized demodicosis: a case report" Journal of Small Animal Practice (2017) 58, pp. 476-479.
McKellar et al., "Clinical and pharmacological properties of ivermectin in rabbits and guinea pigs", The Veterinary Record. 1992, 130(4):71-73; Abstract in 2 pages.
McTier et al., "Discovery of sarolaner: A novel, orally administered, broad-spectrum,isoxazoline ectoparasiticide for dogs", Vet Parasitol. 2016, 222:3-11.
Meadows et al., "A randomized, blinded, controlled USA field study to assess the use of fluralaner tablets in controlling canine flea infestations", Parasit Vectors. 2014, 7:375 in 8 pages.
Medisca Inc., "Doxycycline Hyclate USP—Safety Data Sheet", Jul. 2014, in 6 pages.
Medvedev et al., "Clinical-Laboratory Parallels in Patients with Demodectic Blepharitis at Cosmecevtic's Use", Ophthalmology 2015: 12 (4):50-57.
Merck & Co., Inc., "Stromectol® (Ivermectin) Tablets", Prescription Information, May 2010, in 7 pages.
Merck Animal Health, "Compendium of Veterinary Products—Braveclo@ (fluralaner topical solution) for Dogs," dated Aug. 5, 2019: https://merckusa.cvpservice.com/product/basic/view/1047520 (4 pages).
Merck, "Pyrethrins and Synthetic Pyrethroids" Retreived from: http://www.merckvetmanual.com/pharmacology/ectoparasiticides/ectoparasiticides-used-in-large-animals, downloaded Dec. 11, 2017 in 1 page.
Merial Ltd., "Ivermection—IVOMEC Injection for Cattle and Swine", Material Safety Data Sheet: Jan. 7, 2010, in 7 pages.
Merial Ltd., "NexGard (afoxolaner) Chewables", Safety Data Sheet 2014, in 5 pages.
Merial Ltd., "NexGard (afoxolaner) Chewables", Technical Monograph, 2014, in 21 pages.
Missel et al., "Design and Evaluation of Ophthalmic Pharmaceutical Products", in *Modern Pharmaceutics; 5th Edition* (2009)—Ophthalmic Formulations Guide Chapter 4, pp. 101-189.
Miyajima et al., "Effect of high fat intake on the pharmacokinetic profile of ivermectin in rabbits" Drug Metabolism and Pharmacokinetics 30 (2015): pp. 253-256.
Moser VC., "Amitraz" Encyclopedia of Toxicology, vol. 1, 2014, pp. 200-202.
Mueller et al., "Treatment of canine generalized demodicosis with a 'spot-on' formulation containing 10% moxidectin and 2.5% imidacloprid (Advocate, Bayer Healthcare)", Vet Dermatol. 2009, 20:441-446.
Mueller et al., "Treatment of demodicosis in dogs: 2011 clinical practice guidelines", Vet Dermatol. 2012, 23:86-e21 in 13 pages.
Mueller Ralf S., "Treatment protocols for demodicosis: An evidence-based review", Vet Dermatol. 2004, 15:75-89.
Mullen et al., [Eds.] "Mites (Acari)" in *Medical and Veterinary Entomology*, Academic Press, 2009, 2nd Edition, Chapter 26, p. 549.
Mullens et al., "Comparative in vitro evaluation of contact activity of fluralaner, spinosad, phoxim, propoxur, permethrin and deltamethrin against the northern fowl mite, *Ornithonyssus sylviarum*", Parasit Vectors. 2017; 10:358 in 7 pages.
Murphy et al., "Laboratory evaluation of the speed of kill of lotilaner (Credelio™) against *Ixodes ricinus* ticks on dogs" Parasit Vectors (2017) 10:541 in 8 pages.
Murphy et al., "Laboratory evaluations of the immediate and sustained efficacy of lotilaner (Credelio™) against four common species of ticks affecting dogs in North America", Parasit Vectors. 2017, 10:523 in 8 pages.
Narayanan et al., "Use of Carbodilmides as Stabilizing Agents to Deliver Water—Labile Active Ingredients in Liquid Systems Including Aqueous Medium—Amitraz as a Case Study", J Astm Inter'l., Feb. 2006, 3(2): pp. 1-7.
Nashat et al. "Characterization of Demodex musculi Infestation, Associated Comorbidities, and Topographic Distribution in a Mouse Strain with Defective Adaptive Immunity", Compara Med. 2017, 67(4):315-329.
Nau, Jeffrey. "Oyster Point Pharma", Apr. 12, 2018. PowerPoint in 15 pages.
Nelson et al., "The International Workshop on Meibomian Gland Dysfunction: Report of the Definition and Classification Subcommittee", IOVS, Special Issue. 2011, 52(4):1930-1937.
Ng, Keng Wool., "Penetration Enhancement of Topical Formulations", Pharmaceutics 2018; 10(51) in 3 pages.
Nicholls et al., "*Demodex* species in human ocular disease: new clinicopathological aspects." Int Ophthalmol. Epub May 9, 2016, (Abstract) in 2 pages.
Nicholls et al., "Demodex treatment in external ocular disease: the outcomes of a Tasmanian case series", Springer Science+Business Media Dordrecht, Int Ophtahalmol. 2016, 6 pages.
Nichols et al., "The International Workshop on Meibomian Gland Dysfunction: Executive Summary", IOVS, Special Issue 2011, 52(4):1922-1929.
Nichols Kelly K., "The International Workshop on Meibomian Gland Dysfunction: Introduction", IOVS, Special Issue 2011, 52(4):1917-1921.
Ohmes et al., "Comparative Efficacy of an Imidacloprid/Flumethrin Collar (Seresto®) and an Oral Afoxolaner Chewable (NexGard®) against Tick (*Dermacentor variabilis* and *Amblyomma americanum*) Infestations on Dogs: a Randomised Controlled Trial", Parasitol Res. 2015, 114(Suppl 1):381-94.
Omura et al., "The life and times of ivermectin—a success story", Perspectives, Dec. 2004, 2:984-989.
Ozoe et al., "The antiparasitic isoxazoline443 is a potent blocker of insect ligand-gated chloride channels", Biochem Biophys Res Comm. 2010, 391:744-749.
Pacque et al., "Safety of and compliance with community-based ivermectin therapy", The Lancet, 1990, 335:1377-1380.
Padula et al., "Assessment of the adverse effects of the acaricide amitraz: in vitro evaluation of genotoxicity", Toxicol Mech Methods., 2012; 22(9):657-661.
Palopoli et al., "Global divergence of the human follicle mite *Demodex folliculorum*: Persistent associations between host ancestry and mite lineages" PNAS, Dec. 2015, 112(52):15958-15963.
Panic et al., "Repurposing drugs for the treatment and control of helminth infections", Int J Parasitol Drugs Drug Resist. 2014, 4(3):185-200.
Pass et al., "Pharmacokinetics and metabolism of amitraz in ponies and sheep." J Vet Pharmacol Ther. Jun. 1995; 18(3):210-5, Abstract in 2 pages.
Paterson et al., "Canine generalized demodicosis treated with varying doses of a 2.5% moxidectin + 10% imidacloprid spot-on and oralivermectin: Parasiticidal effects and long-term treatmentoutcomes", Vet Parasitol. 2014, 205:687-696.
Pathan et al., "Chemical Penetration Enhancers for Transdermal Drug Delivery Systems", Trop J Pharm Res. Apr. 2009; 8 (2):173-179.
Pfau Wolfgang, "Azadirachtin Evaluation of Classification and Labelling Proposal with regard to Developmental Toxicity", Report #234379-A2-050601-01 GAB Consulting GmbH, 2014: pp. 1-15.
Piluli.Ru Internet Pharmacy, "Demazol" Instruction Manual, piluli.ru; 2016, in 5 pages.
Powell Frank C., "Rosacea", N Engl J Med. 2005, 352(8):793-803.
PR Newswire, "Elanco Animal Health Announces U.S. Food and Drug Administration {FDA) Approval of Credello® {lotilaner) to Treat and Protect Against Ticks and Fleas", PRNewswire, 2018, in 4 pages.

(56) References Cited

OTHER PUBLICATIONS

Price et al., "An atypical residue in the pore of Varroa destructor GABA-activated RDL receptors affects picrotoxin block and thymol modulation", Insect Biochem Mol Biol. 2014, 55:19-25.
Prohaczik et al., "Safety of fluralaner oral solution, a novel systemic antiparasitic treatment for chickens, in laying hens after oral administration via drinking water", Parasit Vectors. 2017, 10:363 in 7 pages.
Puthran et al., "Ivermectin treatment for massive orbital mylasis in an empty socket with concomitant scalp pediculosis", Indian J Ophthalmol. May-Jun. 2012; 60(3):225-227.
Radakovic et al., "Evaluation of the DNA damaging effects of amitraz on human lymphocytes in the Comet assay", J Biosci. 2013, 38(1):53-62.
Rahman M.M., "Synthesis and Structure-Activity Relationships of Iminopyridazine Competitive Antagonists in Insect GABA Receptors", Doctorate Thesis; Tottori University 2014, in 109 pages.
Ramesh et al., "Kinetics and Hydrolysis of Fenamiphos, Fipronil, and Trifluralin in Aqueous Buffer Solutions", J Agric Food Chem. 1999, 47(8):3367-3371.
Richardson Jill A., "Amitraz", Specific Toxicants (2013), Chapter 31, Section 4: pp. 431-433.
Rios-Yu ii, J.M. et al. (2013). "Evaluation of Demodex folliculorum as a Risk Factor for the Diagnosis ofRosacea In Skin Biopsies. Mexico's General Hospital (1975-201 O)," Indian J. Dermatol. 58: 157.
Robinson et al., "Selamectin versus ivermectin for cheyletiellosis in pet rabbits", in *Clinical Decision Making*; Vet Record, 2016, 178:344-346.
Rodriguez-Dehaibes et al., "Resistance to amitraz and flumethrin in *Varroa destructor* populations from Veracruz, Mexico" J Agricult Res. 2007, 44(3):68-69.
Roeder Thomas, "Pharmacology of the octopamine receptor from locust central nervous tissue (OAR3)" Br J Pharmacol. 1995, 114:210-216.
Rohdich et al., "A randomized, blinded, controlled and multicentered field study comparing the efficacy and safety of Bravecto™ (fluralaner) against Frontline™ (fipronil) in flea- and tick-Infested dogs", Parasit Vectors. 2014, 7:83 in 4 pages.
Romero et al., "Efficacy of fluralaner in 17 dogs with sarcoptic mange", Vet Dermatol. 2016, 27:353-e88 in 4 pages.
Roth C. GmbH, "Carvacrol", Safety Data Sheet CAS #499-75-2; (2015): pp. 1-12.
Rufener et al., "The novel isoxazoline ectoparasiticide lotilaner (Credelio™): a non-competitive antagonist specific to invertebrates β-aminobutyric acid-gated chloride channels (GABACIs)", Parasit Vectors. 2017, 10:530 in 15 pages.
Rufli et al., "The Hair Follicle Mites *Demodex folliculorum* and *Demodex brevis*: Biology and Medical Importance", Dermatologica 1981, 162:1-11.
Rynerson et al., "DEBS—a unification theory for dry eye and blepharitis", Clin Ophthalmol. Dec. 9, 2016, 10:2455-2467.
Sabnis et al., "Topical formulations of metaflumizone plus amitraz to treat flea and tick infestations on dogs", Veterinary Parasitology 150 (2007): pp. 196-202.
Salem, D.A et al. (2013). "Evaluation of the efficacy of oral ivermectin in comparison with ivermectinmetronidazolecombined therapy in the treatment of ocular and skin lesions of Demodex folliculorum,"Int. J. Infect. Dis. 17:e343-e347.
Savla et al., 2020, Tea tree oil for Demodex blepharitis (Review), Cochrane Library, Cochrane Database of Systematic Reviews 2020, Issue 6, Art. No: CD013333, pp. 1-45.
Sánchez-Bayo, "Insecticides Mode of Action in Relation to Their Toxicity to Non-Target Organisms" J Environ Analytic Toxicol. 2011, S4:1-11.
Sanofi Pasteur Inc., "SKLICE® (ivermectin) Lotion", Highlights of Prescription Information, Feb. 2012 in 3 pages.
Santana et al., "A novel technique for improving an in vitro culture of *Demodex* spp (Acari: Demodicidae). A pilot trial." Front. Immunol.
Conference Abstract: Immunocolubia2015—11th Congress of the Latin American Association of Immunology 2015: 2 pages.
Sattler et al., "Reflectance confocal microscopy for monitoring the density of *Demodex* mites in patients with rosacea before and after treatment", Br J Dermatol. 2015, 173:69-75.
Schaub et al., "Monitoring resistance of pear psylla *Cacopsylla pyri* to amitraz" Integrated Fruit Production IOBC/wprs Bulletin, 2001, 24(5):151-153.
Schaumberg et al., "Prevalence of Dry Eye Disease Among US Men", Arch Opthomol., 2009, 127(6):763-768.
Schaumberg et al., "The International Workshop on Meibomian Gland Dysfunction: Report of the Subcommittee on the Epidemiology of, and Associated Risk Factors for, MGD", IOVS, Special Issue 2011, 52(4):1994-2005.
Schear et al., "The Association of Demodex with Chalazia: A Histopathologic Study of the Eyelid", Ophthal Plast Reconstr Surg. 2016, 32(4):275-278.
Schneider et al., "Metrifonate: A Cholinesterase Inhibitor for Alzheimer's Disease Therapy" CNS Drug Reviews, 1999, 5(1):13-26.
Seddiek et al., "The acaricidal efficacy of aqueous neem extract and ivermectin against *Sarcoptes scabiei* var. *cuniculi* in experimentally infested rabbits", Parasitol Res. 2013, 112:2319-2330.
Sedzikowska et al., "Impact of Salvia and Peppermint Oil on the In Vitro Survival of *Demodex* Mites", J Bacter Parasitol. 2015, 6 (3): in 2 pages.
Sharma et al., "Antihelminthic drugs in recurrent apthous stomatitis: A short review", J Pharm Bioallied Sci. 2014, 6(2):65-68.
Sheng et al., "Insecticidal spectrum of fluralaner to agricultural and sanitary pests", J Asia-Pacific Entomol. 2017, 20:1213-1218.
Shin et al., "Changes in the Eye Microbiota Associated with Contact Lens Wearing", mBio. 2016, 7(2): in 6 pages.
Shoop et al., "Discovery and mode of action of afoxolaner, a newisoxazoline parasiticide for dogs" Vet Parasitol. 2014, 201:179-189.
Shtein et al., "Blepharitis", Official reprint from UpToDate® Wolters Kluwer, Jun. 2016, in 19 pages.
Sigel et al., "Structure, Function, and Modulation of GABAA Receptors", J Biol Chem. 2012, 287(48):40224-40231.
Singh et al., "An Update on Therapeutic Management of Canine Demodicosis", Vet World. 2011, 4(1):41-44.
Six et al., "Comparative speed of kill of sarolaner (Simparica™ Chewables) and fluralaner (Bravecto®) against induced infestations of Amblyomma americanum on dogs", Parasit Vectors.. 2016, 9:399 in 7 pages.
Six et al., "Comparative speed of kill of sarolaner (Simparica™) and fluralaner (Bravecto®) against induced infestations of Ctenocephalides felis on dogs" Parasit Vectors., 2016, 9:92 in 7 pages.
Six et al., "Efficacy of sarolaner, a novel oral isoxazoline, against two commonmite infestations in dogs: *Demodex* spp. and *Otodectes cynotis*", Vet. Parasitol. 2016, 222:62-66.
Smith et al., "Demodex musculi Infestation in Genetically Immunomodulated Mice", Compara Med. 2016, 66(4):278-285.
Snyder et al., "Efficacy of lotilaner (Credelio™), a novel oral isoxazoline against naturally occurring mange mite infestations in dogs caused by *Demodex* spp." Parasit Vectors. 2017; 10 (532) in 7 pages.
Sojka Peter A., "Therapeutic Review—Isoxazolines", Author's Accepted Manuscript; Journal of Exotic Pet Medicine: 2018: pp. 1-16.
Sudhakar, Chuppani, "Mange in Sheep and Goats" Retrieved from: http://chuppanisudhakar.blogspot.com/2012/02/mange-in-sheep-and-goats.html; Feb. 5, 2012 in 3 pages.
Suntres et al., "The Bioactivity and Toxicological Actions of Carvacrol" Crit Reviews Food Science Nutri. 2015, 55(3):304-318.
Surface Pharmaceuticals Inc. "Corporate Presentation" Nov. 2017, PowerPoint, in 36 pages.
Szkaradkiewicz et al., "Bacillus oleronius and *Demodex* mite infestation in patients with chronic blepharitis", Clin Microbial Infect 2012, 18:1020-1025; Epub Oct. 22, 2011.
Taenzler et al., "Efficacy of fluralaner administered either orally or topically for the treatment of naturally acquired *Sarcoptes scabiei* var. *canis* infestation in dogs", Parasit Vectors.. 2016, 9:392 in 5 pages.

(56) References Cited

OTHER PUBLICATIONS

Taenzler et al., "Efficacy of fluralaner against Otodectes cynotis infestations in dogs and cats" Parasit Vectors., 2017, 10:30 in 6 pages.
Taenzler et al., "Onset of activity of fluralaner (BRAVECTO™) against Ctenocephalides felis on dogs" Parasit Vectors.. 2014, 7:567 in 4 pages.
Taenzler et al., "Prevention of transmission of Babesia canis by *Dermacentor reticulatus* ticks to dogs after topical administration of fluralaner spot-on solution" Parasit Vectors, 2016, 9:234 in 3 pages.
Taenzler et al., "Prevention of transmission of Babesia canis by *Dermacentor reticulatus* ticks to dogs treated orally with fluralaner chewable tablets (Bravecto™)", Parasit Vectors. 2015: in 6 pages.
Taenzler et al., "The effect of water and shampooing on the efficacy of fluralaner spot-on solution against Ixodes ricinus and Ctenocephalides felis infestations in dogs", Parasit Vectors, 2016, 9:233 in 5 pages.
Tan et al., "Contemporary Asymmetric Phase Transfer Catalysis: Large-Scale Industrial Applications", Org Process Res Dev. 2015, 19:1731-1746.
Tanrattana C., "Practical and update management of canine demodicosis" Thai J Vet Med Suppl. 2017, 47:S55-S56.
Tantiyaswasdikul, P.S., United Nations Fluazuron Summary Report, 2018, Retrieved from: http://www.fao.org/docrep/w8338e/w8338e09.htm: in 20 pages.
Tarr et al., "Case Report: Rectal Administration of Ivermectin to a Patient with Strongyloides Hyperinfection Syndrome", Am J Trop Med Hyg. 2003, 68(4):453-455.
Tater et al., "Canine and feline demodicosis" DVM Magazine 2008: pp. 1-11.
Taylor-Wells et al., "Variations in the Insect GABA Receptor, RDL, and Their Impact on Receptor Pharmacology", in Advances in *Agrochemicals et al. by Gross et al.* [Eds], ACS Symposium 2017, Chapter 1: pp. 1-21.
Tilley et al. [Eds], "Inflammation of the Eyelids (Blepharitis)" Blackwell's Five-Minute Veterinary Consult: Canine and Feline, Fifth Edition 2011, pp. 1-7.
Tomizawa et al., "Neonicotinoid Insecticide Toxicology: Mechanisms of Selective Action", Annu Rev Pharmacol Toxicol. 2005, 45:247-268.
Tomlinson et al., "The International Workshop on Meibomian Gland Dysfunction: Report of the Diagnosis Subcommittee", IOVS, Special Issue 2011, 52(4): 2006-2049.
Toutain et al., "The intravenous and oral pharmacokinetics of lotilaner in dogs", Parasit Vectors. 2017; 10:522 in 8 pages.
Treatment of Demodex Blepharitis with Ivermectin Gel 0.1 % Plus Metronidazole 1 % (2015). ClinicalTrials.gov, ClinicalTrials.gov Identifier: NCT02236403, 5 total pages.
Türk et al., "Comparison of Incidence of Demodex folliculorum on the Eyelash Follicule in Normal People and Blepharitis Patients", Türkiye Parazitoloji Dergisi, 2007, 31(4):296-297.
U.S. Department of Health & Human Services [HHS], "Toxicological Profile for Pyerethrins and Pyrethroids" Pyerethrins and Pyrethroids, 2003, in 328 pages.
UpToDate; Metronidazole (systemic); Drug information; Woters Kluwer, 2016 in 15 pages.
Van Eeden et al., "Solvent and Surfactant Enhanced Solubilization, Stabilization, and Degradation of Amitraz", J Environ Science Health Part B, 2004, B39(1):33-51.
Van Zuuren E.J., "Rosacea", N Engl J Med. 2017, 377(18):1754-1764.
Wall et al., [Eds.] "Chorioptic mange", in *Veterinary Entomology*, Springer Science & Business Media, 1997, p. 341.
Walther et al., "Plasma pharmacokinetic profile of fluralaner (Bravecto™) and ivermectin following concurrent administration to dogs", Parasit Vectors 2015, 8:508 in 5 pages.
Walther et al., "Safety of concurrent treatment of dogs with fluralaner (Bravecto™) and milbemycin oxime—praziquantel", Parasit Vectors 2014, 7:481 in 3 pages.
Walther et al., "Safety of fluralaner chewable tablets (Bravecto™), a novel systemic antiparasitic drug, in dogs after oral administration", Parasit Vectors 2014, 7:87 in 7 pages.
Walther et al., "Safety of fluralaner, a novel systemic antiparasitic drug, in MDR1(-/-) Collies after oral administration", Parasit Vectors 2014, 7:86 in 3 pages.
Walther et al., "Safety of the concurrent treatment of dogs with Bravecto™ (fluralaner) and Scalibor™ protectorband (deltamethrin)", Parasit Vectors. 2014, 7:105 in 2 pages.
Walther et al., "The effect of food on the pharmacokinetics of oral fluralaner in dogs", Parasit Vectors. 2014, 7:84: pp. 1-4.
Wang et al., "Direct nucleophilic difluoromethylation of aromatic isoxazoles activated by electron-withdrawing groups using (difluoromethyl) trimethylsilane" ScienceOpen Research (SOR-CHEM) 2014, pp. 1-7.
Watkins, Thomas. "Lessons abound for dermatologists when animal health and human health intersect." 7pp. Sep. 23, 2017. Dermatology News. Available online at: https://www.mdedge.com/dermatology/article/147784/medica-dermatology/lessons-abound-dermatologists-when-animal-health- and.
Weber et al., "Isoxazolines: A Novel Chemotype Highly Effective on Ectoparasites" ChemMedChem 2016, 11:270-276.
Weller Peter F., "Anthelminthic therapies", UpToDate 2016 (www.uptodate.com); Wolters Kluwer, in 5 pages.
Wengenmayer et al., "The speed of kill of fluralaner (Bravecto™) against *Ixodes ricinus* ticks on dogs", Parasit Vectors. 2014, 7:525 in 4 pages.
White et al., "Controlled Trial and Dose-Finding Study of Ivermectin for Treatment of Onchocerciasis", J Infect Diseases, 1987, 156(3):463-470.
Wikipedia, "Demodex folliculorum" Retrieved from: https://en.wikipedia.org/w/index.php?title=Demodex_folliculorum&oldid=727508589, 2016, in 3 pages.
Williams et al., "A quantitative evaluation of the extent of fluralaner uptake by ticks (*Ixodes ricinus, Ixodes scapularis*) in fluralaner (Bravecto™) treated vs. untreated dogs using the parameters tick weight and coxal index", Parasit Vectors. 2015, 8:352 in 8 pages.
Williams et al., "Fluralaner activity against life stages of ticks using Rhipicephalus sanguineus and Ornithodoros moubata IN in vitro contact and feeding assays", Parasit Vectors. 2015; 8(90): 5 pages.
Williams et al., "Fluralaner, a novel isoxazoline, prevents flea (*Ctenocephalides felis*) reproduction in vitro and in a simulated home environment", Parasit Vectors., 2014, 7:275 in 6 pages.
World Health Organization (WHO), "Trichlorfon" International Programme on Chemical Safety (IPCS) 1992: pp. 1-166.
Yeu, et al., *Safety and Efficacy of Topical Lotilaner 0.25% for the Treatment of Demodex Blepharitis: Results of the Saturn-1 Ph 2b/3 FDA-Pivotal Trial*, presented at ASCRS 2021/SPS-107 Ocular Surface, Jul. 24, 2021.
Yilmaz et al., "Amitraz poisoning, an emerging problem: epidemiology, clinical features, management, and preventive strategies" Arch Dis Child 2003; 88: pp. 130-134.
Youngpradej Monchai, "Efficacy of acaricides in controlling broad mite, *Polyphagotarsonemus latus* (Banks) under laboratory and pot test conditions" Retrieved from : http://agris.fao.org/agris-search/search.do?recordID=TH2000002880; 1998 in 2 pages.
Zegans et al., "Considerations in Understanding the Ocular Surface Microbiome", Am J Ophthalmol. 2014, 158(3):420-422.
Zhang et al., "Discovery of an orally bioavailable isoxazoline benzoxaborole (AN8030) as a long acting animal ectoparasiticide", Bloorg Med Chem Lett. 2015, 25:5589-5593.
Zhang et al., "Optimization of isoxazoline amide benzoxaboroles for identification of a development candidate as an oral long acting animal ectoparasiticide" Bioorganic & Medicinal Chemistry Letters 26 (2016): pp. 3182-3186.
Zhang, Alexis Ceecee, et al., "Ocular Demodex: a systematic review of the clinical literature", Department of Optometry and Vision Sciences, Ophthalmic* Physiological Optics, The Journal of the College of Optometrists, Opthalmic Physiol Opt 2020, pp. 1-44.
Zhao et al., "Association of Blepharitis with *Demodex*: A Meta-analysis", Ophthal Epidemiol. 2012, 19(2):95-102.
Zhao et al., "Insect γ-Aminobutyric Acid Receptors and Isoxazoline Insecticides: Toxicological Profiles Relative to the Binding Sites of

(56) References Cited

OTHER PUBLICATIONS

[H]Fluralaner, [$^3$H]-4'-Ethynyl-4-n-propylicycloorthobenzoate, and [$^3$H]Avermectin", J Agri. Food Chem. 2014, 62:1019-1024.
Zhao, Y.E. et al. (2012). "A meta-analysis of association between acne vulgaris and Demodexinfestation," J. Zhejiang Univ. Sci. B. 13: 192-202.
Zheng et al., "Kinetics and mechanism of the hydrolysis of imidacloprid", Pestic Sci. 1999, 55:482-485.
Zhu et al., "Effect of viscosity on tear drainage and ocular residence time", Optom Vis Sci. Aug. 2008:85(8):715-725; Abstract in 2 pages.
Zoetis, Revolution Plus® (selamectin and sarolaner topical solution) Prescribing Information, Oct. 2018, available at: https://www.zoetisus.com/_locale-assets/pdf/revolution-plprescribing-information.pdf (accessed Jul. 13, 2020) in 2 pages.
Bandyopadhyay et al., 2010, Development of Ophthalmic formulations, in Nema et al., eds., Pharmaceutical Dosage forms: Parenteral Medications, Third Ed. vol. 1: Formulation and Packing, pp. 255-286.
Carmignani et al., 2002, Ophthalmic vehicles containing polymer-solubilized tropicamide: "in vitro/in vivo" evaluation, Drug Development and Industrial Pharmacy, 28(1): 101-105.
Cavalleri et al., Jul. 13, 2018, Laboratory evaluation of the efficacy and speed of kill of lotilaner (Credelio™) against ixodes ricins ticks on cats, Parasites & Vectors, 11:413, 10 pp.
CDC, Mar. 30, 2019, Lyme Disease, retrieved from the Wayback Machine on Jan. 26, 2023, https://web.archive.org/web/20190330184401/https://www.cdc.gove/lyme/index.html.
CDC. Diseases Transmitted by Ticks. Retrieved from the internet on May 8, 2023, https://www.cdc.gov/ticks/diseases/index.html#:-: text=Lyme%20disease%20is%20transmitted%20by,pacificus)%20along%20the%20Pacific%20coast. (Year: 2023).
Chhadva et al., 2017, Meibomian glad disease, American Academy of Ophthalmology, pp. S20-S26.
Drugs.com. Credelio (lotilaner). Retrieved from the internet on May 8, 2023, https://www.drugs.com/vet/credelio-lotilaner.html. Published Sep. 2019. (Year: 2019).
Holgado et al., 2020, Contact lenses drug-delivery systems: a promising therapeutic tool, Archivos de la Sociedad Espanola de Oftalmologia (English Edition), 95(1):24-33.
Kono et al., 2022, State-dependent inhibition of GABA receptor channels by the ectoparasiticide fluralaner, Pesticide Biochemistry and Physiology, 181,:105008.
Lee et al., 2015, Comparison of cytotoxicity and wound healing effect of carboxymethylcellulose and hyaluronic acid on human corneal epithelial cells, Int. J. Ophthalmot. 8(2):215-221.
Lo Re et al., Apr. 15, 2004, Identifying the vector of Lyme disease, Am Fam Physician, 69(8), 3 pp.
Mayo Clinic, 2022, Blepharitis, https://www.mayoclinic.org/diseases-conditions/blepharitis/symptoms-causes/syc-20370141.
Merriam-Webster. Prevent. Retrieved from the internet on May 11, 2023, https://www.merriam-webster.com/dictionary/prevent. (Year:2023).
Pubchem, Aug. 2022, Polyoxyl 35 castor oil, CID 154733643, 24 pp.
Pubchem. Fluralaner. Retrieved from the Internet on Aug. 18, 2023.8/23/2 https://pubchem.ncbi.nlm.nih.gov/compound/25144319 (Year:2023).
Sprong et al., Mar. 6, 2018, Control of Lyme borreliosis and other ixodes ricinis-borne diseases, Parasites & Vectors, 11(1):145, 16 pp.
Yeu et al., 2022, Lotilaner ophthalmic solution, 0.25%, for the treatment of demodex blepharitis: results of a prospective, randomized, vehicle-controlled, double-masked, pivotal trial (saturn-1), Cornea, 00:1-9.
Avila et al., 2021, Topical ivermectin-metronidazole gel therapy in the treatment of blepharitis caused by *Demodex* spp.: A randomized clinical trial, Contact Lens and Anterior Eye, 44:101326, 6 pp.
Collett et al., Jun. 2, 2016, Dosage regimens, https://basicmedicalkey.com/dosage-regimens/, 7 pp.
Environmental Protection Agency [EPA], 1996, "Amitraz Approval Summary", in 182 pages.
Foster et al., 2017, "Fipronil (Frontline Top Spot)", Information on Use Sheet, etc. in 2 pages.
Foster et al., Jun. 20, 2017, "The Use of Fipronil (Frontline Top Spot) in Dogs and Cats", from www.peteducation.com in 4 pages.
G Production Inc., Oct. 2011, Metrogel® (metronidazole) Gel: Highlights of Prescribing Information in 2 pages.
Hecht et al., Dec. 2019, Permethrin cream for the treatment of demodex blepharitis, Cornea, 38(12):1513-1518 (abstract).
Sigma-Aldrich, "Ivermectin Product Specification", Prod No. I8898—Sigma-Aldrich.com, accessed 2019, 1 page.
US Food and Drug Administration, Jan. 26, 2022, Inactive ingredients in approved drug products search: frequently asked questions, www.fda.gov/drugs/drug-approvals-and-databases/inactive-ingredients-approved-drug-products-search-frequently-asked-questions, 6 pp.
Wang et al., 2020, Peribulbar injection of glucocorticoids for thyroid-associated ophthalmopathy and factors affecting therapeutic effectiveness: a retrospective cohort study of 386 cases, Experimental and Therapeutic Medicine, 20:2031-2038.
Zelczak Todd A., Mar. 25, 2017, Closing the Lid on Blepharitis, PowerPoint presentation, MOS 2017 Cleveland Seminar, 41 pages.
Zoetis U.S., 2019, "Terramycin® Ophthalmic Ointment", Patient Order Form downloaded from URL: <https://www.zoetisus.com/products/cats/terramycin-ophthalmic-ointment.aspx.>, in 2 pages.

* cited by examiner

PHARMACEUTICAL COMPOSITIONS FOR DEMODEX RELATED BLEPHARITIS AND EYELID CRUSTING

TECHNICAL FIELD

The present invention relates to the formulation of ectoparasiticidal and antibiotic compositions into topical pharmaceutical compositions useful for the treatment of eyelid inflammation, in particular demodex related blepharitis and eyelid crusting. This invention also relates to a topical pharmaceutical composition suitable for the treatment of mammalian ectoparasites.

DESCRIPTION OF BACKGROUND AND/OR RELATED AND/OR PRIOR ART

Blepharitis represents one of the most common anterior segment disorders encountered in ophthalmology. Blepharitis produces a red-rimmed appearance at the margins of the eyelids. It affects both the upper and lower eyelids. Blepharitis tends to recur and can become chronic.

Blepharitis is inflammation usually involving the part of the eyelid where the eyelashes grow. The eyes can eventually become red, itchy and irritated, with dandruff-like crusts appearing on the eyelashes (also known as "crusting"). It may also result in loss of lashes.

Recent studies show that ophthalmologists and optometrists observe blepharitis in approximately 37% to 47% of their patients. Despite the prevalence of blepharitis in both presentation and contribution to ocular conditions, there is little data on how eye care practitioners treat the disease.

A number of causes for blepharitis exist, including bacterial infections, parasitic infestation, viral infection and autoimmune conditions. Infective causes including bacteria and parasites are likely to be the most common causes. There are two types of blepharitis, i.e. anterior and posterior blepharitis. Anterior blepharitis is a condition where the outside front edge of the eyelids is inflamed, where the eyelashes are attached. Posterior blepharitis is a condition where the moist inside part of the eyelid is affected.

The traditional treatment for blepharitis consists of lid hygiene, and the application of a variety of "proprietary" cleansers. The goal is to control the disease and its underlying causes, maintain vision and to avoid secondary complications. However, many chronic cases persist. Demodex mites have been thought to be an etiologic factor in many cases of anterior blepharitis with lid margin debris. Demodex infestations are commonly treated with systemic and topical administration of parasiticides. For example, ocular demodex can be treated by performing a daily eyelid margin scrub with diluted shampoo alone or in combinations with a mercury oxide ointment, a metronidazole gel, or a pilocarpine gel applied to the base of the eye lashes. However, these treatments frequently fail to eradicate the demodex parasite and the infestation persists.

U.S. Pat. No. 8,128,968 teaches a composition containing about 0.6% to about 20% of tea tree oil to treat ocular demodex infestations and related conditions. Tea tree oil treatments, however, suffer from several disadvantages. Tea tree oil can easily lead to eye irritation and cause stinging sensations. Even a small amount will induce tearing, if it reaches the ocular surface. Due to the reflex tearing, dilution occurs and efficacy is reduced. Owing to the possibility of severe irritation, some eye centres carry out clinic based treatments, where the tea tree oil is professionally applied by an eye doctor. Tea tree oil compositions for home applications are thinner, which has little or perhaps no effect on the demodex mite population.

U.S. Pat. No. 5,952,372 teaches the use of treating demodex with oral administration of ivermectin. More specifically, oral ivermectin in a regimen of 200 micrograms per kilogram body weight per dose for 2 or 3 consecutive doses are given to the patient, at least 3 and not more than 7 days apart. Oral tetracycline was also given to the patients through consistent intermediate stages. However, this is an expensive medication regimen and requires repeated dosing. In our experience, a single dose, as used in some centers, does not eliminate the demodex mites. This is likely due to the pharmacokinetic properties of the ivermectin being partitioned into the various body compartments, with low concentrations at the specific target site.

Alternatively, U.S. Pat. No. 5,952,372 teaches topical ivermectin compounded to a 2% concentration by weight in a cream, lotion, or gel carrier vehicle as a treatment for all clinical stages and signs of rosacea in affected persons. However, this is only in relation to using a single active agent, ivermectin, for the treatment of a general dermatological condition such as rosacea, rather than specifically targeting blepharitis.

Demodex mites have also been found to be associated with various bacteria, including *Bacillus oleronius*. It is therefore possible that other bacteria play a role in the pathogenic process. Demodex mites killed by tea tree oil or via oral administration of ivermectin usually disintegrate on the ocular surface and release a variety of associated organisms, which probably explains why, in our experience, a proportion of patients continue to suffer the usual symptoms of blepharitis, despite eradication of the demodex mites.

DETAILED DESCRIPTION

The aim of this invention is to overcome blepharitis, by eliminating demodex mites and/or other associated bacteria.

The demodex species are microscopic, obligate, elongated mites which belong to the family "Demodicidae" of the order *Acari* of the class Arachnida. Demodex folliculorum and demodex brevis are found parasitizing on the human body surface. Demodex folliculorum occupies the hair follicles and upper sebaceous glands, whilst demodex brevis exists principally in the depth of the sebaceous glands [source: "*A meta-analysis of association between acne vulgaris and Demodex infestation*" by Ya-e Zhao, Li Hu, Li-Ping Wu, Jun-xian Ma, J Zhejiang Univ Sci B. 2012 March; 13(3):192-202].

This invention contains a parasiticidal agent such as ivermectin, and an antibiotic such as oxytetracycline, or any other tetracycline or macrolide antibiotic. Other types of antibiotics are also suitable, such as fluoroquinolones and aminoglycosides. Tetracycline antibiotics comprise a class of anti-microbials with applications in human and veterinary medicine, and are among the most heavily used antibiotics in the world. The purpose of antibiotics is to kill harmful bacteria, where possible, or to at least reduce their proliferation with bacteriostatic compounds.

The pharmaceutical composition according to the invention are suited for treating blepharitis and may be in liquid, pasty form, and more particularly in the form of creams, ointments, milks, pomades, powders, impregnated pads, syndets, towelettes, solutions, gels, sprays, foams, suspensions, lotions, sticks, shampoos, or washing bases.

In a preferred embodiment of this invention, the pharmaceutical composition according to the invention is in the form of an emulsion of the cream. In this embodiment, the compositions according to the invention are in the form of an emulsion. Most simple emulsions are oil-in-water, which means that the oil droplets are suspended in a continuous water phase, whereas others are water-in-oil. Emulsions can be classified as either oil-in-water (O/W) or water-in-oil (W/O) emulsions, depending on whether oil or water is the dispersed phase. Milk, cream and sauces are some examples of oil-in-water emulsions. O/W emulsion is preferred in this embodiment, where oil molecules are dispersed in water. Water therefore evaporates more readily from O/W emulsion. There are also more complicated emulsions that are used to enhance the delivery and stability of certain active ingredients. The choice of emulsification system is therefore highly dependent on the choice of ingredients comprised in the cream. Cream, regardless if it is cold cream, emollient cream, day cream, night cream, medicated cream, etc, all have the same basic emulsion formulation. The effectiveness of the cream further depends on the emulsion type and pH, as well as the type of oils, fats, alcohols and esters used.

In the above preferred embodiment of this invention, sorbitol is used as a humectant, so that the cream will not "dry out" when exposed to the atmosphere for prolonged periods of time. It also assists in maintaining phase stability, such as preventing separation of the aqueous and non-aqueous components.

The other Ingredients used in this embodiment of the invention are determined by referring to the Cosmetic Ingredient Review ("CIR"), or any other toxicological reports, where available, so as to ensure that these chosen ingredients are suitable for topical application and have lower risk of causing ocular irritation. The CIR was established in 1976 by the industry trade association (then the Cosmetic, Toiletry, and Fragrance Association, now the Personal Care Products Council, located in the United States of America), with the support of the U.S. Food and Drug Administration and the Consumer Federation of America. Although funded by the Council, CIR and the review process are independent from the Council and the cosmetics industry.

In this embodiment, emulsifying wax is used. There are several varieties of emulsifying wax available. Some are synthetically produced and some are vegetable-derived. This embodiment uses vegetable-based emulsifying wax NF (which means that it conforms to the specifications of the National Formulary, or "NF"), which is from naturally occurring fats and esters, derived from cetostearyl alcohol. Emulsifying wax (NF) is also suitable for most skin types as allergic reactions and skin sensitivities have rarely been recorded, in relation to such waxes.

According to the Final Report on the Safety Assessment of Fossil and Synthetic Waxes, International Journal of Toxicology (May/June 1983, 3: 43-99), concentrations of the Emulsifying Wax NF in the range of 1%-10% are found in typical use in skin cream. The ocular irritation of Emulsifying Wax NF was also studied in rabbits (according to the Draize method). The "Draize Test" is an acute toxicity test devised in 1944 by the Food and Drug Administration toxicologists John H. Draize and Jacob M. Spines. Initially used for testing cosmetics, the procedure involves applying 0.5 mL or 0.5 g of a test substance to the eye or skin of a restrained, conscious animal, and then leaving it for a set amount of time before rinsing it out and recording its effects. The Draize Test has since become an endorsed method to evaluate the safety of materials meant for use in or around the eyes.

According to the Amended Safety Assessment of Alkyl Esters as Used in Cosmetics, Cosmetics Ingredient Review (Apr. 12, 2013), Ethylhexyl Stearate is safe for use and the undiluted test material was at most mildly irritating to rabbit skin. In a 6-day cumulative skin irritation study, an undiluted test material (which had a mean maximum irritation index (MMII) of 0.67) was poorly tolerated, whereas a 10% aqueous solution (which had a MMII of 0.33) was relatively well tolerated. In human testing, a formulation containing 7.6% of Ethylhexyl Stearate was not an irritant or sensitizer (56 subjects), and not phototoxic (10 subjects), and not a photosensitizer (27 subjects), although some slight reactions were reported in the photosensitisation study. The undiluted test material did not provoke any significant injury in the rabbit's eyes (max Primary irritation Index (PII) 4.67/100 at 1 h). The Report stated that the reproductive toxicity of 2-ethyl-1-hexanol was already addressed in a fetotoxicity study (performed on diethylhexyl adipate); it was suggested that the fetotoxicity reported for mice in that study was actually due to a zinc deficiency and that given the extent of 2-ethyl-1-hexanol absorption and the load that would be expected to enter the hepatic circulation, the potential for 2-ethyl-1-hexanol-induced reproductive toxicity was not thought to be an issue.

According to the report: Safety Assessment of Cyclomethicone, Cyclotetrasiloxane, Cyclopentasiloxane, Cyclohexasiloxane, and Cycloheptasiloxane, International Journal of Toxicology (30 (Supplement 3)), rats were exposed to up to 700 ppm (0.07%) of Cyclopentasiloxane via inhalational (environmental) exposure for 5 days per week, for 12 months and 24 months respectively, and no eye lesions were found.

In the report: Safely Assessment of Tocopherols and Tocotrienols as Used in Cosmetics, Cosmetics Ingredient Review (Apr. 4, 2014), it was reported that tocopheryl acetate was not irritating to rabbit eyes in one study, but it produced weak to moderate conjunctival irritation in another study (European Chemicals Agency. 3,4-dihydro-2, 5, 7, 8-tetramethyl-2-(4, 8, 12-trimethyldecyl)-2H-benzopyran-6-yl acetate). Undiluted tocopheryl acetate was instilled into the conjunctival sac of 3 Vienna White rabbits, and the eyes were not rinsed. The eyes were scored at 1, 24, 28, and 72 h after instillation. Slight irritation was observed at 1-48 h, and the eyes were normal at 72 h. In a modified Draize Test, the same protocol was followed, and undiluted dl-α-tocopherol was instilled into the eyes of six rabbits; again, the eyes were not rinsed. Weak to moderate conjunctival irritation (i.e., redness) was observed, which subsided by day 7. No corneal changes were reported.

Although mild irritation is shown in the studies by the European Chemical Agency (while some others showed no irritation), this embodiment of the invention uses diluted tocopheryl acetate.

According to the Final Report on the Safety Assessment of EDTA (Ethylenediaminetetraacetic acid), calcium disodium EDTA, diammonium EDTA, dipotassium EDTA, disodium EDTA, TEA-EDTA, tetrasodium EDTA, tripotassium EDTA, trisodium EDTA, HEDTA, and trisodium HEDTA, International Journal of Toxicology, (21 (Supplement 2); 95-142, 2002), Disodium EDTA was classified as a non-irritant in a primary mucous membrane irritation test using rabbit eyes. EDTA of approximately 0.5% to 1% is not toxic when added to balanced salt solutions.

According to the Final Report on the Safety Assessment of Methylisothiazolinone and Methylchloroisothiazlinone, Journal of the American College of Toxicology (Volume 11, Number 1, 1992). Methylisothiazolinone and Methylchloroisothiazlinone (MI/MCI) were evaluated for ocular irritation in eight Draize or modified Draize tests using albino rabbits. MI/MCI-886 ranging in concentration from 1.1% to 14% active ingredient (a.i.) and MI/MCI-GC with a 1.5% a.i. concentration were corrosive when tested as supplied. However, aqueous dilutions of MI/MCI-886 with concentrations of 0.056% a.i. were non-irritating; 0.28% a.i. was slight to moderately irritating; 0.56% and 1.7% a.i. were moderately to severely irritating: and 2,8% and 5,6% a.i. were severely irritating (corrosive).

As this invention is to be used topically, good absorption is achieved by using Propylene Glycol as a solvent for the ivermectin. According to the Cosmetic Ingredients Report Panel Meeting on Jun. 28-29, 2010, the ocular irritation of Propylene Glycol was determined using groups of 6 males and female New Zealand white albino rabbits. Undiluted Propylene Glycol was found to be a slight eye irritant. In this embodiment, Propylene Glycol is therefore diluted by approximately 10 times, and is therefore non-irritating to the eye, as seen in the our experimental studies on the patients.

The selection of the ingredients depends very much on the final purpose and the desired consistency (for example, creamy, hard, soft, greasy, or dry) of the invention. Changing one ingredient may also require changes in many others, if the physical characteristics of the invention are to be maintained.

Based on the abovementioned reports and scientific researches, various ingredients were selected for this invention.

According to one embodiment of the invention, the compositions comprise the following range (by weight):
  ivermectin (1 to 5%)
  an antibiotic such as oxytetracycline, and/or other tetracycline, macrolide, fluoroquinolone, or aminoglycoside antibiotic. (1 to 5%)
  water (45 to 65%)
  emulsifying wax NF (Cetearyl Alcohol, Polysorbate 60, PEG—150 Stearate, and Steareth-20) (5% to 15%)
  ethylhexyl stearate (5% to 15%)
  cyclopentasiloxane (0.01% to 0.05%)
  sorbitol (1 to 10%)
  tocopheryl acetate (0.01% to 0.5%)
  disodium EDTA (0.01% to 0.1%)
  propylene glycol (3% to 10%)
  methylchloroisothiazolinone and methylisothiazolinene (0,001% to 0.01%).

The pharmaceutical composition according to the preferred embodiment is in the emulsion of a cream. In another embodiment, the invention is in the form of an ointment. A cream is a preparation of a medication for topical use that contains a water base. Essentially, it is a preparation of oil in water. An ointment is a preparation of a medication for topical use that contains an oil base, which is essentially a preparation of water in oil.

In another embodiment, the pharmaceutical composition according to the invention which is in the form of an ointment, which comprise the following range (by weight):—
  ivermectin (1-5%)
  tetracycline (1-5%)
  sorbitan monooleate (span 80) (3-5%)
  light mineral oil (10%-15%)
  petrolatum (70%-80%)

Whether in the form of a cream or ointment, the pharmaceutical composition according to the invention is therefore formulated in a way that it does not cause eye irritation, even if a small amount reaches the ocular surface. This invention therefore allows patients to apply such medication themselves, without having to go to a clinic. Patients may be able to continuously repeat the dosage over a period of time, so as to ensure a lower risk of recurrence of blepharitis.

In this invention, the topical application of the cream or ointment allows the ivermectin and antibiotic to be applied directly to the affected area, thus overcoming the problem associated with oral application of ivermectin being partitioned into the various body compartments, consequently with low concentrations at the specific target site. The direct topical application of the cream or ointment onto the affected area also minimises the risk of medication-related side effects felt in other parts of the body.

The cream or ointment is applied to the eyelids, in particular to eyelashes and the base of the eyelashes.

The cream or ointment may also be used to treat other conditions. It was mentioned in "A meta-analysis of association between acne vulgaris and Demodex infestation", published in 2012, that there is evidence (including one meta-analysis) which suggests a connection between acne vulgaris and demodex. There is also other evidence which suggests a relationship between acne rosacea and demodex. For example, an earlier publication, Severe Demodex folliculorum-associated Oculocutaneous Rosacea In A Girl Successfully Treated With Ivermectin (JAMA Dermatol 2014 January; 150(1):61-3) reported the case of a 12-year old girl who was successfully treated with oral ivermectin. Other reports include Correlation Between Serum Reactivity To Demodex-associated *Bacillus Oleronius* Proteins, and Altered Sebum Levels and Demodex Populations in Erythematotelangiectatic Rosacea Patients (J Med Microbiol 2014 February; 63 (Pt 2): 258-72, Evaluation of Demodex Folliculorum As A Risk Factor for the Diagnosis of Rosacea in Skin Biopsies (Indian J Dermatol. 2013 March, 58(2):157, Potential Role of Demodex Mites and Bacteria in the Induction of Rosacea (J Med Microbiol 2012 November; 61 (Pt 11): 1504-10), and Correlation Between Ocular Demodex Infestation and Serum Immunoreactivity to *Bacillus* Proteins in Patients with Facial Rosacea (Ophthalmology 2010 May: 117(5): 870-977). Accordingly, this invention may be used to treat other medical conditions as well.

The cream or ointment is topically administered every night to the affected areas, for the treatment of blepharitis and/or acne, to obtain the appropriate and desired treatment outcome, by using a clean finger or cotton bud. For example, the invention is to be applied in a light and gentle rubbing action across the base of the eyelashes by first closing the eyes and applying to the upper eyelid eyelash bases/roots, and then looking upwards so that the invention can be applied to the lower eyelid eyelash bases/roots. The invention is left on the affected area overnight.

The invention is then removed with normal cleansing water in the morning, for a month, so as to avoid early recurrences from new generations of mites which may emerge from unaffected eggs.

EXAMPLES

The following examples are merely illustrative, and not limitative of the remainder of the disclosure in any way whatsoever. These examples are illustrative of the effectiveness of the invention.

Several patients had itching in the eyes and crusting around the eyelids. The presence of demodex mites was then confirmed. The confirmation was done by gently pulling on the eyelashes, and then transferring the presenting demodex mites onto a piece of cellophane tape. The said cellophane tape was then affixed onto a microscope slide. These demodex mites were viewed at 100 times of magnification, and counted to determine the mite density per lash follicle.

In treating the affected patients, the eyelids were first cleaned with hot compresses and a clean towel to remove all crusts and debris. The cream or ointment was then applied directly onto the affected area, by using a clean finger or a cotton-tipped applicator. The cream or ointment covered the entire eyelashes and roots.

The cream or ointment was left on the affected area for the entire night, and then washed away in the morning. This process was repeated on a nightly basis, for a month. The patients were then re-assessed for the presence of demodex mites, and no demodex mites were found on the eyelash roots of any patients. Before the treatment, many patients experienced itching on the eyelid margins. These patients were free of any symptoms, at the 1-month follow up.

Some cases were treated solely with ivermectin. However, these studies also demonstrate the necessity of antibiotics, in some cases.

Example 1

This 52 year old Chinese gentleman had a long history of facial skin rashes that occurred along the nasolabial fold (also commonly known as "smile lines" or "laugh lines") as well as around the ears. He had previously been treated by dermatologists for a diagnosis of seborrhoeic dermatitis with various creams including topical steroids. He presented with increasing crusting around the eyelashes and intermittent eye irritation. On examination, erythematous macules and papules were noted along the glabellar area as well as the nasolabial folds bilaterally. Marked crusting and many demodex mites were found in the eyelash follicles. A sample retrieved from one eyelash revealed 5 demodex folliculorum in the single follicle. He was treated with Ivermectin (only comprising 1%) cream nightly to the eyelid margins (as prescribed), as well as the inflamed areas of his face. One month later the eyelid margin crusting had resolved, as had the facial rash. No demodex mites were found in the eyelash follicles after the treatment.

Example 2

This 44 year old Caucasian gentleman had recurring redness of the eyes associated with itching and burning sensations for the past 6 years. On examination, eyelash crusting together with lid margin erythema and many demodex mites were seen. He was first treated with oral Ivermectin (Stromectol) 12 mg and was advised to do scrubs using Tea Tree Oil on the eyelids twice a day. Over the next 2 months, the demodex mites reduced in numbers but were not completely eliminated, despite 4 subsequent doses of oral Ivermectin and continuing Tea Tree Oil scrubs. Tea Tree Oil applications were also performed on the patient. Owing to the persistence of the mites, dosages of Ivermectin (1%) cream was prescribed instead. After nightly applications of this cream for one month (as prescribed), no demodex mites were seen in the eyelash follicles and his ocular inflammation had markedly improved.

Example 3

This 28 year old Chinese gentleman had recurring redness on the left eyelids for the past 9 years and had been treated previously with a variety of topical antibiotics including Framycetin. On examination, he had asymmetric disease, with severe inflammation of the left eyelid margins and corneal punctate erosions. Some demodex mites were seen in the eyelash follicles. He was treated with a combination of Ivermectin (1%) cream as well as Tetracycline eye ointment to the eyelids. Oral Doxycycline 100 mg twice a day was prescribed. Demodex mites resident in the lash follicles were eradicated alter 1 month of nightly Ivermectin cream applications, as prescribed. Although eyelid inflammation was reduced, it was not entirely eliminated and the topical and oral tetracycline treatment was continued for the next 2 months. 4 months after initial presentation, the eyelids were much improved and inflammation had subsided. He was followed up for 2 years, and during this time remained free of severe episodes of eye or eyelid inflammation. A mild recurrence of demodex infestation was noted at the second year mark, and this was treated successfully with a further course of Ivermectin (1%) cream.

What is claimed is:

1. A method for the treatment of demodex blepharitis and eyelid crusting, comprising:
   identifying a presence of demodex mites in eyelash follicles of an individual;
   topically administering every night for a month onto the eyelash follicles of the individual in need of such treatment and removing with water in the morning, a topical pharmaceutical composition formulated as an emulsion, comprising:
     an effective amount of ivermectin and an additional antibiotic selected from the group consisting of a tetracycline, an oxytetracycline, a macrolide, a fluoroquinolone, an aminoglycoside and metronidazole;
     water;
     a humectant comprising sorbitol;
     a mixture of emollients comprising cyclopentasiloxane and ethylhexyl stearate;
     an additional agent as emulsifier;
     a mixture of preservatives comprising methylchloroisothiazolinone and disodium EDTA;
     an antioxidant comprising tocopheryl acetate; and
     a solvent comprising propylene glycol;
   wherein the topically administering is sufficient to eliminate the presence of demodex mites in the eyelash follicles of the individual.

2. The method defined by claim 1, wherein said ivermectin is present in the range of 1 to 5% by weight of the topical pharmaceutical composition.

3. The method defined by claim 1, wherein said additional antibiotic is present in the range of 1% to 5% by weight of the topical pharmaceutical composition.

4. The method defined by claim 1, wherein said additional antibiotic is a tetracycline antibiotic.

5. The method defined by claim 1, wherein said additional antibiotic is a macrolide antibiotic.

6. The method defined by claim 1, wherein said additional antibiotic is a fluoroquinolone antibiotic.

7. The method defined by claim 1, wherein said additional antibiotic is an aminoglycoside antibiotic.

* * * * *